(12) United States Patent
Ruby et al.

(10) Patent No.: US 9,554,754 B2
(45) Date of Patent: Jan. 31, 2017

(54) SYSTEM, METHOD AND COMPUTER PROGRAM FOR WEIGHT, LIFESTYLE AND/OR DISEASE MANAGEMENT INTEGRATING NUTRITION, EXERCISE AND BEHAVIOUR MANAGEMENT

(76) Inventors: Jeffrey Ruby, Toronto (CA); Louis Pèrusse, Lac Saint-Joseph (CA); Karyn Hood, Toronto (CA); Mary Bamford, Toronto (CA); Jean-Jacques Dugoua, Toronto (CA); Natasha Vani, Toronto (CA)

( * ) Notice: Subject to any disclaimer, the term of this patent is extended or adjusted under 35 U.S.C. 154(b) by 0 days.

(21) Appl. No.: 12/713,911

(22) Filed: Feb. 26, 2010

(65) Prior Publication Data

US 2011/0172497 A1 Jul. 14, 2011

Related U.S. Application Data

(60) Provisional application No. 61/293,436, filed on Jan. 8, 2010.

(51) Int. Cl.
| | | |
|---|---|---|
| *G06F 19/00* | (2011.01) | |
| *A61B 5/00* | (2006.01) | |
| *A63B 24/00* | (2006.01) | |
| *G06Q 50/22* | (2012.01) | |
| *G01G 19/414* | (2006.01) | |

(52) U.S. Cl.
CPC ......... *A61B 5/7264* (2013.01); *A63B 24/0075* (2013.01); *G06F 19/345* (2013.01); *G06F 19/3475* (2013.01); *G06F 19/3487* (2013.01); *G06Q 50/22* (2013.01); *A61B 5/4866* (2013.01); *G01G 19/4146* (2013.01)

(58) Field of Classification Search
None
See application file for complete search history.

(56) References Cited

U.S. PATENT DOCUMENTS

| | | | | |
|---|---|---|---|---|
| 5,673,691 A | * | 10/1997 | Abrams et al. | 600/300 |
| 6,269,339 B1 | * | 7/2001 | Silver | 705/2 |
| 2003/0204412 A1 | * | 10/2003 | Brier | 705/2 |
| 2004/0029684 A1 | * | 2/2004 | Zarif | 482/8 |
| 2004/0267565 A1 | * | 12/2004 | Grube | 705/2 |
| 2005/0228691 A1 | * | 10/2005 | Paparo | 705/2 |
| 2009/0070141 A1 | * | 3/2009 | Jolley et al. | 705/2 |

(Continued)

OTHER PUBLICATIONS

Frayling, Timothy M., et al. "A common variant in the FTO gene is associated with body mass index and predisposes to childhood and adult obesity." Science 316.5826 (2007): 889-894.*

(Continued)

*Primary Examiner* — William Thomson
*Assistant Examiner* — Davin Sands
(74) *Attorney, Agent, or Firm* — Milller Thomson LLP; Eugene Gierczak

(57) ABSTRACT

A system, method and computer program for integrated, personalized disease management is provided. The method involves capturing individual attributes, analyzing the individual attributes to establish an individual classification for an individual, and based on the individual classification for the individual assigning automatically a program template for disease management of the individual. The system provides a coaching platform for managing interactions between a coach and a system client based on the program template.

22 Claims, 11 Drawing Sheets

(56) References Cited

U.S. PATENT DOCUMENTS

| | | |
|---|---|---|
| 2009/0131814 A1* | 5/2009 | Thompson .................... 600/561 |
| 2010/0098809 A1* | 4/2010 | Bender et al. .................. 426/87 |
| 2010/0105038 A1 | 4/2010 | Draper et al. |
| 2010/0160117 A1* | 6/2010 | White et al. ...................... 482/9 |
| 2010/0179833 A1* | 7/2010 | Roizen et al. .................... 705/3 |

OTHER PUBLICATIONS

Loos, Ruth JF, et al. "Common variants near MC4R are associated with fat mass, weight and risk of obesity." Nature genetics 40.6 (2008): 768-775.*

Noble, Ernest P., et al. "D2 dopamine receptor gene and obesity." International Journal of Eating Disorders 15.3 (1994): 205-217. (abstract only).*

* cited by examiner

SYSTEM, METHOD AND COMPUTER PROGRAM FOR WEIGHT, LIFESTYLE AND/OR DISEASE MANAGEMENT INTEGRATING NUTRITION, EXERCISE AND BEHAVIOUR MANAGEMENT

PRIORITY

This application claims the benefit of U.S. Patent Application Ser. No. 61/293,436 filed Jan. 8, 2010.

FIELD OF THE INVENTION

The present invention relates to weight, lifestyle and/or disease management. The present invention relates more particularly to technology for weight, lifestyle, and/or disease management.

BACKGROUND

Poor diet/nutrition and insufficient exercise is resulting in significant population segments being overweight and in poor health. This is increasing health costs and dissatisfaction of individuals with their weight, health and self-image, which in turn is a contributor to loss of productivity and depression.

Current diet and preventive programs appear to be ineffective. While significant monies are spent on diet-related solutions and fitness, existing methods are not producing the desired improvements in health and well being.

Similar problems exist in disease management or prevention. Effective management or prevention of disease generally requires adherence by individuals to specific behaviour including treatment and lifestyle regimens (including nutrition, exercise, rest, etc.). More and more resources are being spent on disease prevention, and even more so on disease management, incorporating lifestyle elements; however, the results produces by these programs are generally less than adequate.

A significant contributor is that current methods do not adequately address the need for effective, personalized behaviour modification, and furthermore the regime that is likely to produce results for an individual has been shown to be dependent on various individual factors, and yet solutions that produce personalized programs are relatively uncommon, or if they exist they generally involved personalized analysis, coaching and training, which however is generally quite expensive. Furthermore, in the areas of disease management (the term being used generally to include weight management), an integrated approach to all behaviours associated with the disease management goals is required, yet existing methods generally fail to take such an integrated approach.

Even in relation to personalized approaches based on personal assessments and personal coaching, prior art solutions do not address the fact that better results and lasting results have been shown to be produced if there is a good personality match between the client and the coach.

People are busier and busier, and for this and other reasons appear to be less able to make the time investment generally required to reach and maintain disease management goals. Scheduling regular coaching or training based on in person meetings becomes a real obstacle, and has a limiting effect on the ability to meet disease management goals.

Genetic testing is now available to assess predisposition for developing a disease, and even susceptibility to weight gain, based on the individual's genetic makeup. Yet, integration of genetic testing in disease management or prevention regimens is relatively rare.

There is a need for a method that addresses the shortcoming of current approaches and technologies to disease management. There is a particular need for a system that leverages technology to automate aspects of disease management in order to produce better behaviour modification results and make personalized disease management more affordable and accessible.

SUMMARY

The present invention provides a computer-implementable method for integrated and personalized management of nutrition, fitness and/or behaviour for the purpose of disease management, the method comprising: (a) capturing nutrition, fitness and/or weight management related attributes or behaviours of an individual, or individual attributes; (b) analyzing the individual attributes and matching of the individual attributes to one of a plurality of nutrition, fitness, behavioural and/or weight management classifications, or individual classification, each individual classification being associated with a program template that defines personal lifestyle program aspects that are likely to deliver positive results for the individual based on his/her individual classification, or program template, by operation of a computer; and (c) based on the matching of the individual attributes to the individual classification, and thereby to the associated program template, automatically establishing a nutrition, fitness, and/or weight management program for the individual.

The present invention also provides a computer-network implementable system for personalizing a nutrition, fitness and weight management program, the system comprising: (a) a network-accessible application server operable to: (i) capture one or more individual attributes defined by nutrition, fitness and/or weight management related attributes related to an individual; (ii) match the individual attributes to one of a plurality of individual classifications, each individual classification being associated with a program template defining nutrition, fitness and weight management program aspects; and (iii) establish for the individual a personalized nutrition, fitness, and/or weight management program based on the program template; and wherein at least one network-connected client is operable to enable the individual to provide the one or more individual attributes and access the personalized nutrition, fitness, and/or weight management program.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

DETAILED DESCRIPTION

The present invention provides a system, method and computer program for management of weight, lifestyle, and/or disease, integrating nutrition, fitness and behaviour management. The present invention further integrates genetic evaluation into management of weight, lifestyle, and/or disease.

Figure 2:
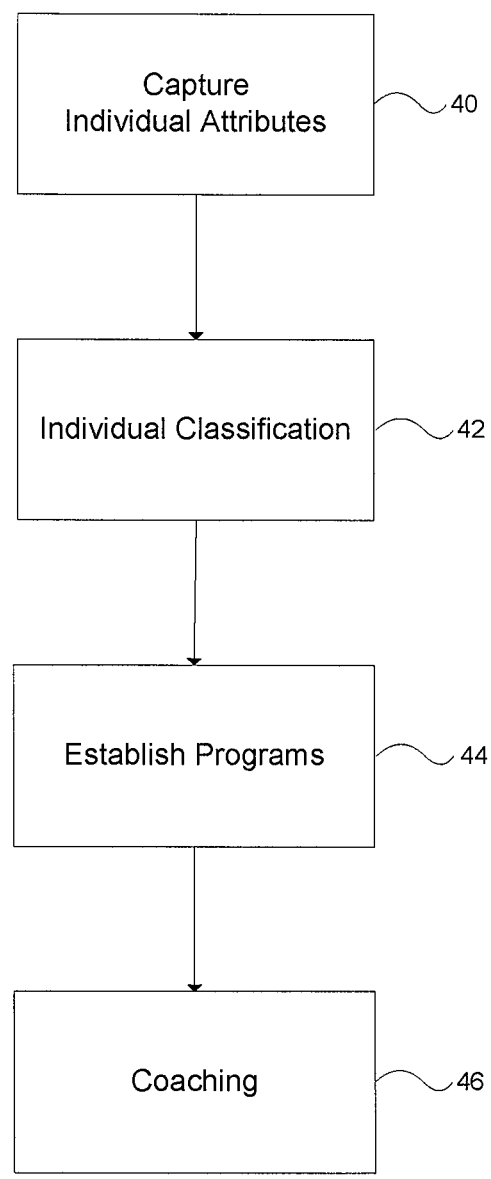
FIG. 2 is a workflow diagram illustrating aspects of the disease management assessment method of the invention.

FIG. 2 illustrates a method in accordance with an aspect of the present invention. One aspect of the invention is a computer system, method and computer program that enables integrated and personalized management of nutrition, fitness and behaviour for the purpose of disease management (which for the purpose of the present disclosure includes weight management). The invention more specifically enables (1) capture (40) of nutrition, fitness and/or weight management related attributes or behaviours of an individual ("individual attributes") to define a "profile", and (2) analysis of the individual attributes and matching of the individual attributes to one of a plurality of nutrition, fitness, behavioural and/or weight management classifications ("individual classification") (42), each individual classification being associated with a program template that defines personal lifestyle program aspects that are likely to deliver positive results for the individual based on his/her individual classification ("program template"), and (3) based on the matching of the individual attributes to the individual classification, and thereby to the associated program template, automatically establishing a nutrition, fitness, and/or weight management program (44) for the individual.

In another aspect of the invention, the individual classification is based on a combination of a plurality of categorizations of the individual based on their individual attributes. In yet another aspect of the invention, the categorizations include one or more of nutrition categorizations (e.g. caloric intake), exercise intensity categorizations (e.g. beginner, intermediate, advanced), exercise location categorizations (e.g. home-based or gym-based), and behavioural attributes relative to nutrition, fitness, and/or weight management (e.g. "Emotional", "Disconnected", "All or None"). The permutation of the categorizations defines a set of individual classifications, which determine the selection of an effective program template.

In another aspect of the invention, the computer platform includes or is linked to a coaching platform. The coaching platform manages the interaction between an individual and a coach selected for that individual. In an aspect of the invention the matching of an individual and his/her coach is made based on the individual's behaviour attributes. In another aspect of the invention, the lifestyle assessment includes questions directed at establishing an individual's personality traits; coaches are evaluated for their personality traits; and the matching of an individual and a coach occurs based on compatibility of their respective personality traits. It should be understood that the term "coach" is used generally and may include a personal trainer, lifestyle coach, health care professional etc.

The coaching platform provides the individual with access (46) to an outline of the steps required to achieve their nutrition, fitness, and/or weight management program with the assistance and/or oversight of a coach. The coaching platform is operable to monitor progress of the individual based on the program requirements. The coaching platform is operable to guide the coach, and through the interactions between the coach and the individual that are in part facilitated by the coaching platform, the individual through the program requirements.

Figure 3:
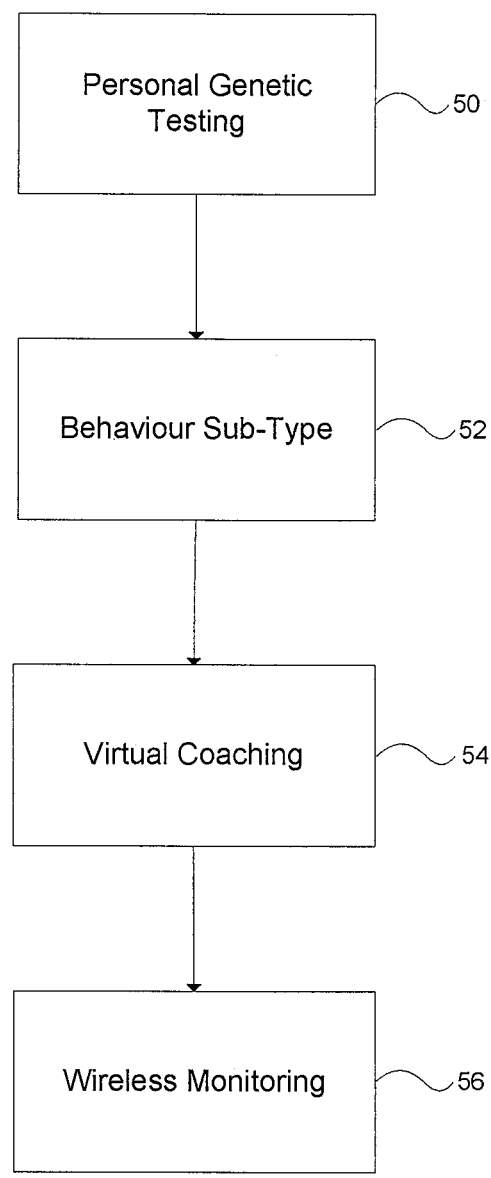
FIG. 3 is a further workflow diagram illustrating further aspects of the method of the present invention.
Figure 4:
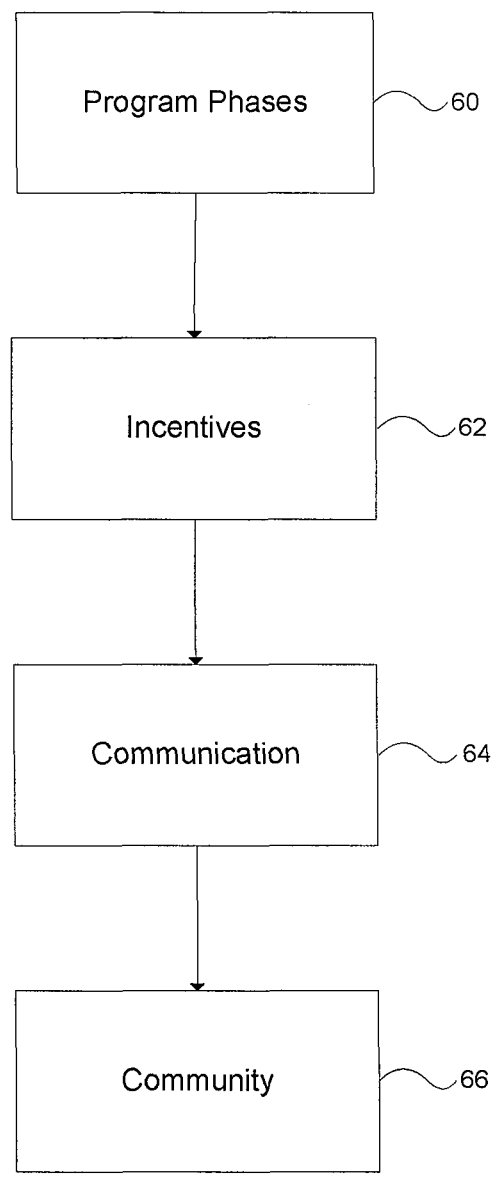
FIG. 4 is a further workflow diagram illustrating still further aspects of the method of the present invention.

FIGS. 3 and 4 illustrate further aspects of a method of the invention.

The program requirements may include three phases (60) including an (i) educational component (educational content provided via the multimedia platform regarding nutrition, exercise, and behaviour management approaches to achieve the individual's program goals), (ii) activation component (weight loss targeting based on specific program directions), and (iii) celebrate component (celebrating achievement of interim goals and targeting of sustainable weight management).

In another aspect of the invention, the individual attributes also relate to nutrition and/or fitness related genetic markers for an individual, established using one or more genetic tests (50), to produce genetic tests results for the individual. The genetic tests may relate to testing for the FTO gene, the MC4R gene, and/or the DRD2 gene. The genetic test results may be used to as further individual attributes that in turn define the selection of the program template. Alternatively, the nutrition, fitness and/or weight management program attributes may be further personalized based on the genetic test results, including automatically by providing the genetic test results to the coaching platform. It should be understood that the genetic testing and behavioral traits are not limited to the genes or the personality profiles described herein.

In another aspect of the invention, the coaching platform is operable to manage the award of incentives (62) to the individual based on performance to interim goals or otherwise adhering to program requirements. The incentives may include financial incentives for attending coaching sessions, reaching lifestyle milestones, and/or providing new client referrals.

The coaching platform is further linked to or includes an interface to enable virtual coaching. Virtual coaching (54) enables coaches to provide real-time web-based coaching based on the individual's program template. The interface may further enable the coach to provide audio and/or video instruction in real-time to the individual, for example by means of a web cam.

The coaching platform is further linked to or includes a messaging platform. The messaging platform enables the coaches to provide regular feedback and encouragement (64) to their clients via a variety of media including email, SMS, IM, FACEBOOK™, TWITTER™, other electronic networking messaging means, and phone calls. Some of the messages may be sent automatically by operation of the messaging platform, or generated automatically but customizable by the coaches, or may require creation by the coach.

In another aspect of the invention the coaching platform includes or is linked to a community utility that is operable to create one or more social networks for individuals to interact with one another (66) in order to provide motivation, support, and encouragement in meeting their respective program goals.

In another aspect of the invention, the computer platform includes a wireless data capture utility that is operable via a wireless gateway to interface with one or more wireless devices associated with the individual such that the individual may provide information or updates (56) regarding their nutritional or exercise related activities. The computer platform is operable to save such information or updates to a database that is linked to the coaching platform, such that the information or updates are accessible via the associated client area and coaching area.

As explained above, behavioural attributes may be used (52) by the system of the present invention to automatically generate directions and/or suggestions to the individual classification based on a combination of a plurality of categorizations of the individual based on their individual attributes. These categorizations include one or more of nutrition categorizations (e.g. caloric intake), exercise intensity categorizations (e.g. beginner, intermediate, advanced), exercise location categorizations (e.g. home-based or gym-based), and behavioural attributes relative to nutrition, fitness, and/or weight management (e.g. "Emotional", "Disconnected", "All or None"). These categorization are determined by the analysis engine (32) based on information obtained by operation of the capture utility (28).

The permutation of the categorizations defines a set of individual classifications, which determine the selection of an effective program template.

System

Figure 1:
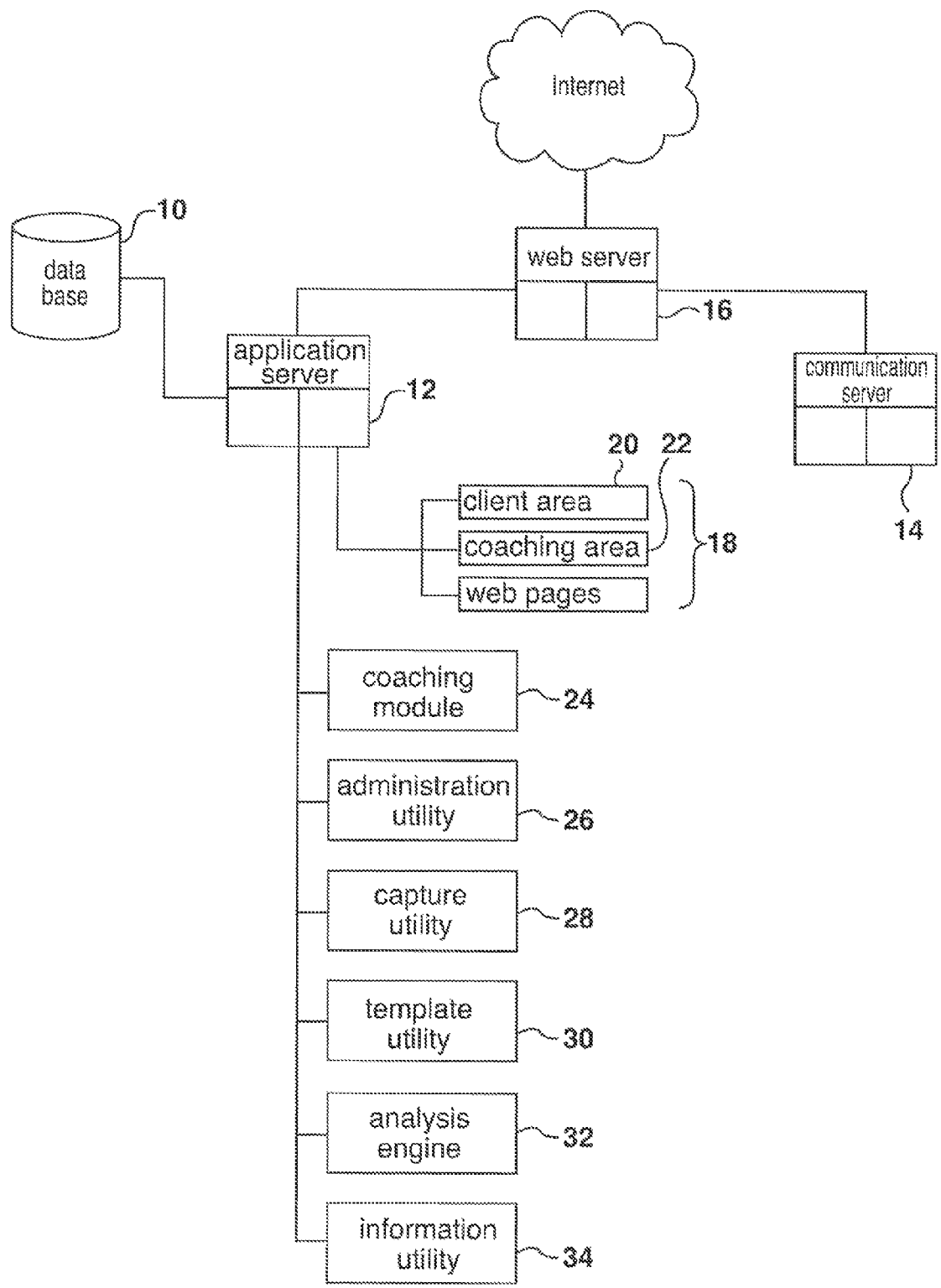
FIG. 1 illustrates a system in accordance with present invention.

FIG. 1 illustrates a system in accordance with present invention, referred to herein as the disease management system. The disease management system may include a database (10) and application server (12) linked to a communication server (14) and a web server (16). The communication server (14) and web server (16) are linked to a network, such as the Internet. The application server (12) includes one or more software modules that provide the functionality described in this disclosure, in co-operation in some cases with the database (10). The application server (12) further co-operates with the web server (16) so as to define a series of web pages (18) accessible via the Internet, based on access parameters defined by the operator of the web server (16) (referred to as the "operator"). These web pages (18) generally define the following web areas including a set of interrelated web pages and associated system functions supported by the application server (12): a client area (20), accessible by a plurality of clients of the operator, enabling the clients (referring to an "individual"—as described above, who is a client of the operator) to access the various client-directed functions of the system described in this disclosure, and a coaching area (22), provisioned by the coaching platform or coaching module (24) of the application server (12).

The various system users, including clients and coaches may access system of the present invention via the web server (16) and web access through a network, for example by using a smart phone, desktop or laptop computer, or mobile device. The application server includes an administration utility (26) that enables the operator to administer the functions of the system, and define the access to data (through the database (10)) or functions of the application server (12) that the users shall have access to. The administration utility (26) is used to create sign-in requirement for particular users to the web server (16) which may include various means of identifying users, including username/password. The administration utility (26) for example is operable to ensure that coaches have access to data pertaining only to the clients with whom they have been matched, that clients can access only their own data, and other aspects of privacy of data and identity are maintained.

The database (10) and application server (12) are further linked to track in the database (10) activities of clients in order to enable the functions of the coaching platform (24).

The web pages (18) define a series of web interfaces that enable the various users of the system to interact with the functions and utilities of the application server (12).

The system illustrated in FIG. 1 enables the integrated and personalized management of nutrition, fitness and behaviour for the purpose of disease management described in this disclosure. The application server (12) includes a capture utility (28) that enables the operator to create a series of web interfaces for collecting information regarding clients, including related to their individual attributes. The capture utility (28) for example may implement a form creator for establishing one or more web forms or questionnaires that require clients to supply specific personal information such as information regarding the nutrition, fitness and/or weight management related attributes or behaviours of the client, which are then stored to the database (10). The administration utility (26) and database (10) are configured such that the access to a client's personal information is only available to those authorized by the client, such as their coach.

The administration utility (26) may be configured to present to each client various permissions or consents that may be required to signify the client's agreement to the collection and use of their information.

The application server (12) further includes a template utility (30) that enables the operator to create and update the various program templates used by the system.

The application server (12) further includes an analysis engine that is operable to supper the various analytical functions described in the present invention, for example the matching of the individual attributes to the individual classifications, so as to match a particular client to a particular program template and thereby automatically establish, by operation of the system, a disease management program for the client (which may includes nutrition, fitness, weight management or other aspects).

The web pages (18) define a series of web interfaces that enable the various users of the system to interact with the functions and utilities of the application server (12). Examples of these web interfaces are illustrated in FIGS. 5a, 5b, 5c, 5d, 5e, and 5f.

For example, as shown in FIGS. 5a through 5f, the individual may access their personalized nutrition, fitness, and/or weight management program via a web interface. The interface may provide on each web page a set of basic personal program information (78), such as the individual's name, current phase of the program, program week, current weight and goal or target weight. The interface may also provide on each screen quick links to often used web pages, including for example "My Profile" (70) (to access or input the individual's attributes), "Scheduling" (72) (to view the schedule for the program), "Lifestyle Profile" (74) (to access or input lifestyle factors), and "Genetics" (76) (for enabling the user to provide genetic test results or view current genetic test results).

Figure 5A:
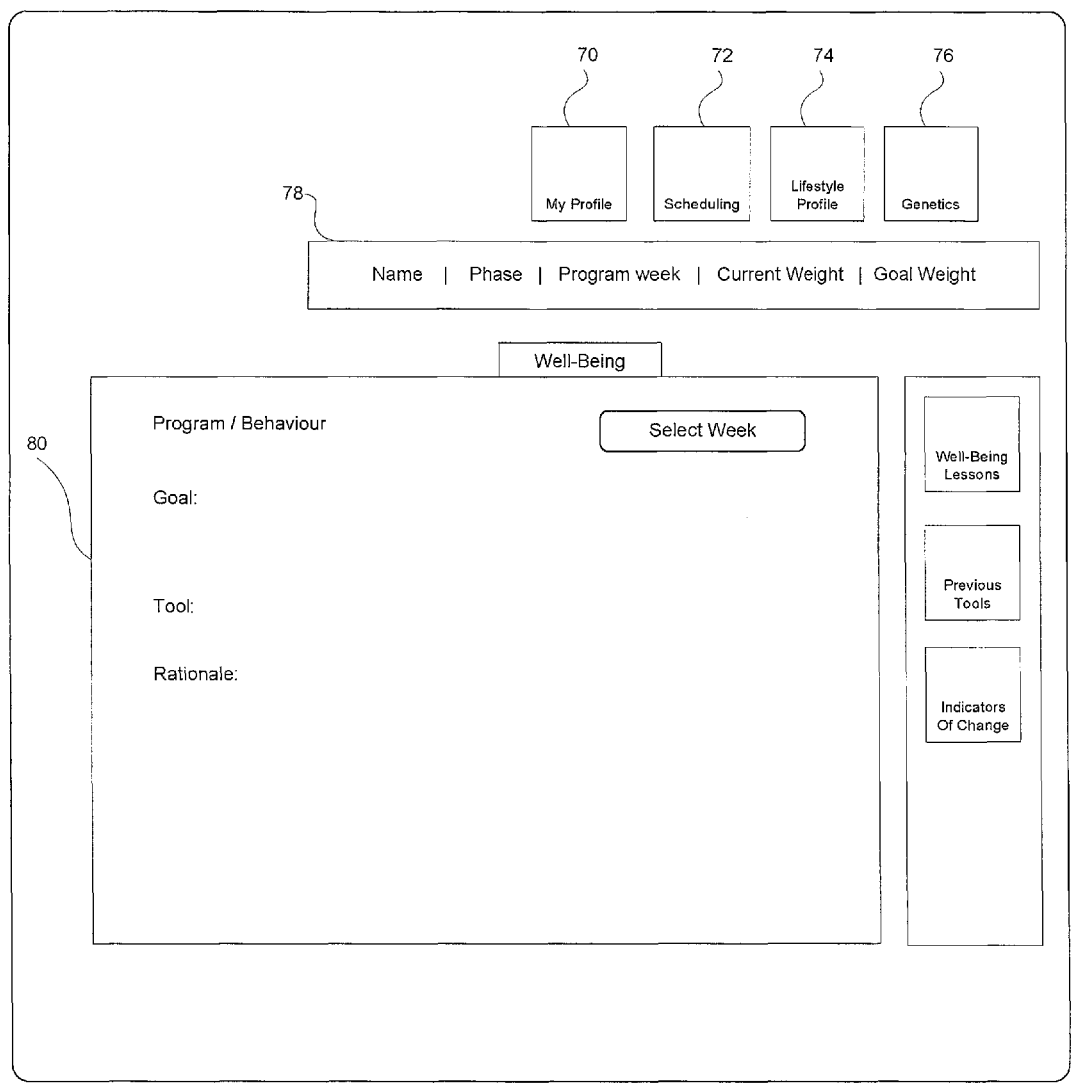
FIGS. 5a, 5b, 5c, 5d, 5e, and 5f are a series of screenshots that illustrate possible web interfaces enabled by the present invention.

One web interface, as shown in FIG. 5a, may be directed towards providing the individual with access to an outline of their personalized program portal (80). The personalized program portal may include web pages corresponding to well-being lessons for each week (e.g. tracking changes), other tools, indicators of change, etc. For example, well-being lessons may reference the individual's behavioural categorization as well as a summary of their weekly goal, the tool by which to achieve the goal, and a rationale for establishing the goal. The rationale may be a detailed explanation of why the goal, which may serve as further encouragement for the individual to commit to achieving the goal.

The outline of the personalized program portal (80) may also include a selection for the week of the program to outline. This enables an individual to forecast further goals to prepare them mentally for the upcoming weeks. The individual may also access the well-being lessons, tools, indicators of change, etc. from the personalized program portal (80) to navigate to alternate pages related to the personalized program.

The genetics web page may enable the individual to provide genetic test results. The genetics web page may also provide a breakdown of the significance of the genetic tests. For example, for the FTO gene, the web page may provide an explanation to the user that:

FTO gene is the most important and frequent "obesity" gene identified so far. The function is unclear, but widely expressed in body fat tissue and in regions of the brain involved in the regulation of energy balance. The variant you have been tested for is associated with a 2-fold increased risk of weight gain and obesity, but this risk is reduced in physically active subjects.

If the gene is present (either one or two), exercise recommendations move from the base line recommendations to vigorous recommendations which consist of an increase in duration, frequency and intensity (as measured by the RPE scale) in the client cardiovascular program.

If the FTO gene is not present, client cardiovascular recommendations remain at base line.

Similarly, for the MC4R gene, the web page may provide an explanation to the user that:

MC4R regulates appetite and food intake by initiating a satiety signal. Subjects carrying the variant you have been tested for are at risk of weight gain and obesity because they eat more and consume a higher proportion of their calories from dietary fat.

If the gene is present (either one or two), the client will move from their original basic program at their appropriate calorie level, to the balanced program at their appropriate calorie level which will limit the clients dietary fat intake.

If the MC4R gene is not present, the client will continue to follow the basic nutrition plan at their appropriate calorie level, including: Basic 45% Carbohydrate, 22% Protein, 33% Fat; Balanced 45% Carbohydrates, 25% Protein, 30% Fat.

Similarly, for the DRD2 gene, the web page may provide an explanation to the user that:

DRD2 regulates dopamine, the primary chemical messenger of pleasure in the brain, which is involved in a broad range of addictive behaviours. The reward properties of food are reduced in subjects carrying the variant you have been tested for, which may lead to compulsive eating.

If the DRD2 gene is present (either one of two), clients well being program will be for the emotion based subtype.

If the DRD2 gene is not present, the client will follow the Well Being program that was assigned for them in their initial assessment.

Figure 5B:
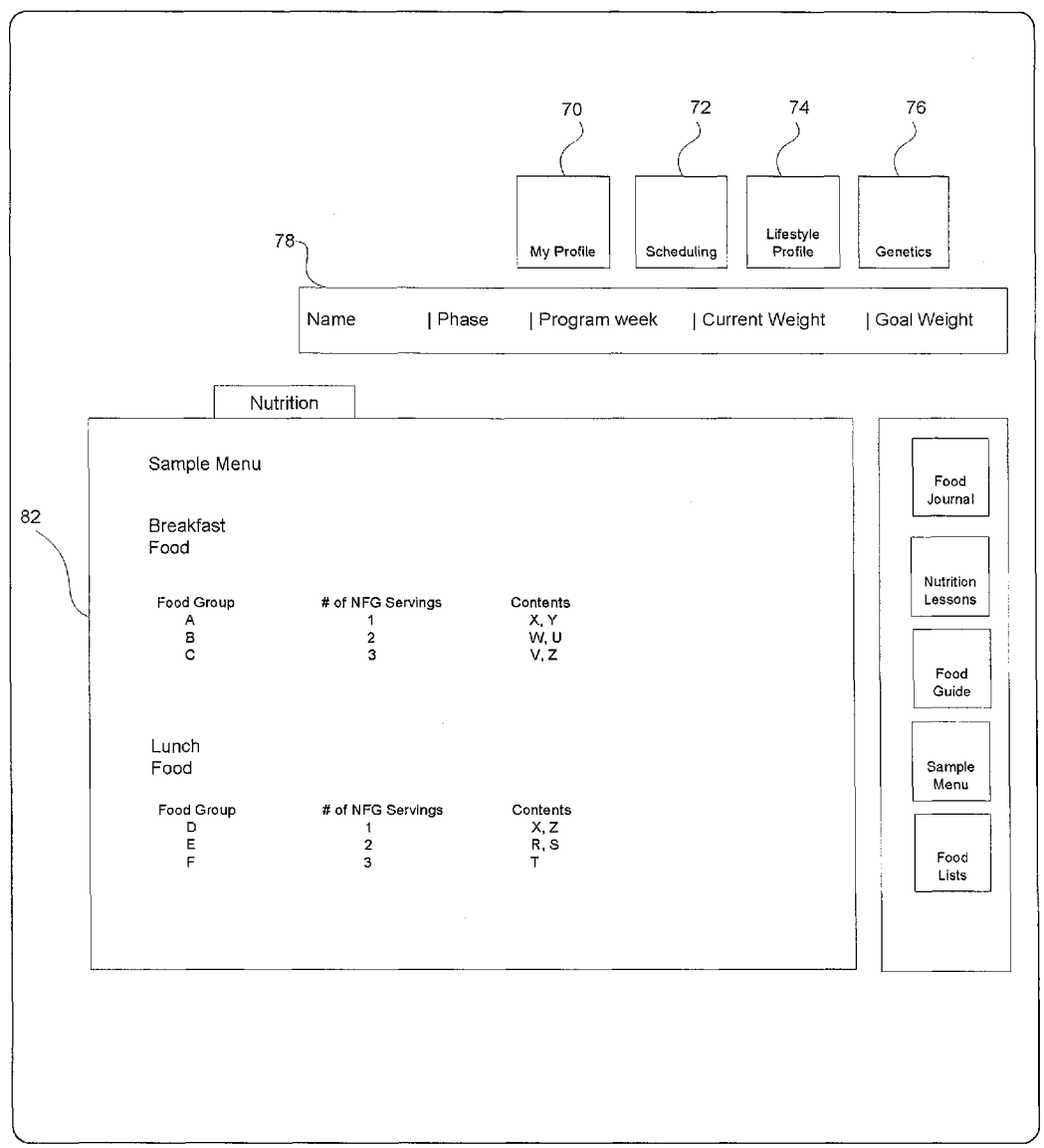

Another web interface, as shown in FIG. 5b, may be directed towards providing the individual with access to a nutrition portal (82) for regulating their diet in accordance with the program. The nutrition portal may include web pages corresponding to a food journal (discussed further below), nutrition lessons, food guide (discussed further below), sample menu, food lists, etc. For example, as shown, the sample menu may provide the individual with a breakdown of meals and may include a summary of the food to be consumed (e.g. A, B, C), the number of servings to be consumed (e.g. 1, 2, 3, etc.) and a summary of the contents of the food (e.g. X, Y; W, U; V, Z) for educational purposes. The individual may also access the food journal (discussed further below), nutrition lessons, food guide (discussed further below), sample menu, food lists, etc. from the nutrition portal (82) to navigate to alternate pages related to the nutrition portal.

Figure 5C:
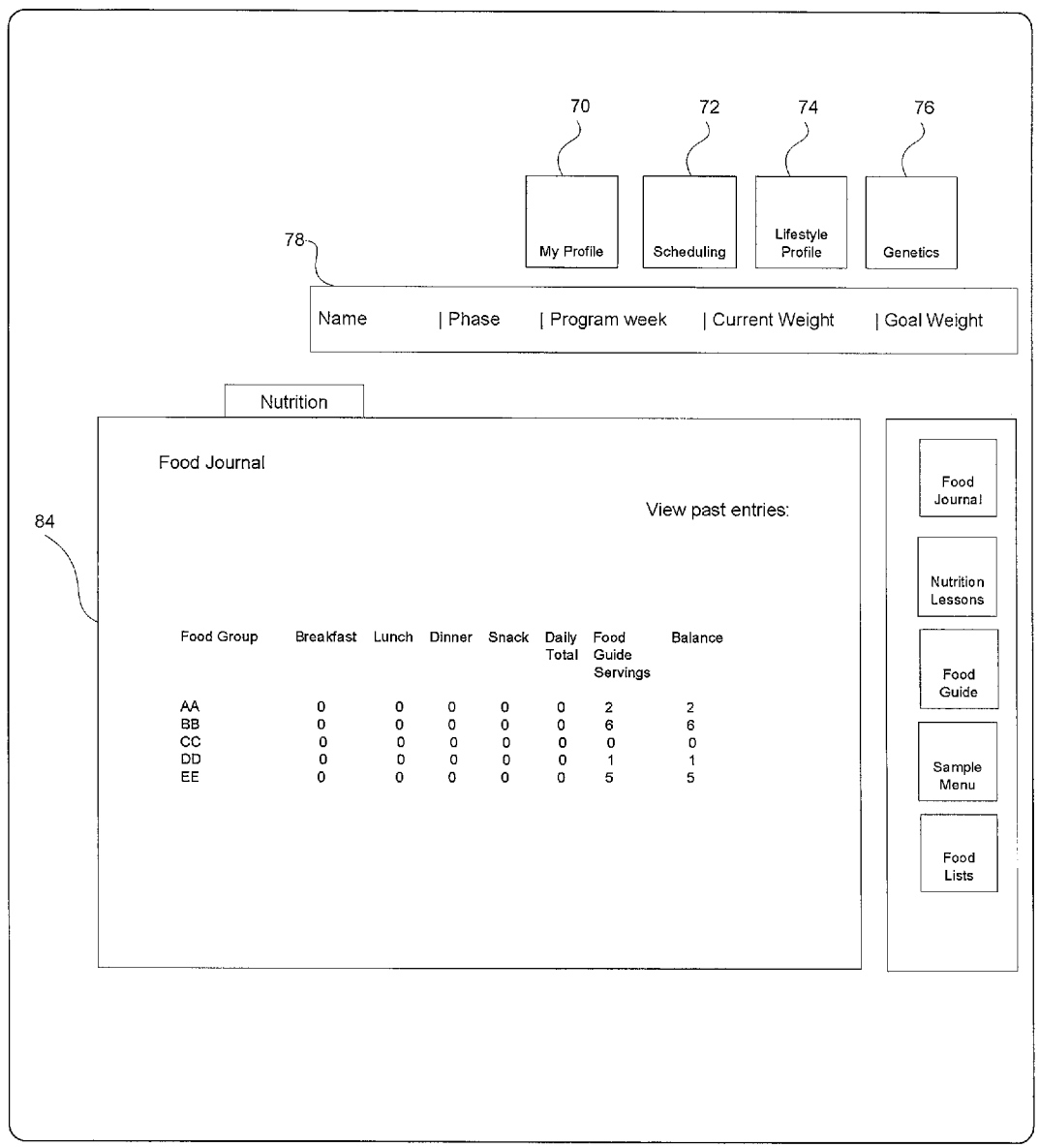

An example of a food journal web page (84) is shown in FIG. 5c. The food journal may include a table that provides pre-filled rows, each for one of the food groups (e.g. AA, BB, CC, DD, EE, etc.) prescribed by the program. Columns of the table may correspond to meals and snacks for each day, week, etc. The table enables the individual to input, or fill in, the number of servings of each food group per meal. The table then determines the total number of daily servings of each of the good groups and compares the total to a predetermined number of servings required based on the food guide to provide the balance to the individual, enabling the individual to easily determine where additional consumption is required or over consumption has occurred. Examples of food guides are provided in Tables 1 and 2.

The web interface may display to the individual whether they are eating within the optimal range of each food group as determined by the food guide.

TABLE 1

Example Food Guide

Food Guide Break Downs
Basic-45% Carbohydrate, 22% Protein, 33% Fat

|  | Cals | Protein | Carbs | Fat | Fiber | 1200 cal | 1400 cal | 1600 cal | 1800 cal | 2000 cal | 2200 cal |
| --- | --- | --- | --- | --- | --- | --- | --- | --- | --- | --- | --- |
|  |  |  |  |  |  | Recommended number of servings/day | | | | | |
| Free Vegetables 10 | 10 | 1 | 3 | 0 | 1.5 | 6 | 6 | 6 | 6 | 6 | 6 |
| Sweet Vegetables 50 | 50 | 2 | 10 | 0 | 2 | 1 | 1 | 0 | 0 | 0 | 0 |

TABLE 1-continued

Example Food Guide

| | | | | | | | | | | | |
|---|---|---|---|---|---|---|---|---|---|---|---|
| Starchy Vegetables 100 | 100 | 3 | 21 | 0 | 2.5 | 0 | 0 | 1 | 1 | 1 | 2 |
| Fruit 50 | 50 | 1 | 11 | 0 | 2 | 2 | 3 | 3 | 4 | 5 | 5 |
| Whole Grains | 100 | 3 | 18 | 1..5 | 2 | 3 | 3 | 4 | 4 | 5 | 5 |
| Milk and Alternatives 100 | 100 | 8 | 15 | 1 | 0 | 2 | 2 | 1 | 1 | 1 | 1 |
| Milk and Alternatives 150 | 150 | 10 | 16 | 5 | 0 | 0 | 0 | 1 | 1 | 1 | 1 |
| Meat and Alternatives 100 | 100 | 17 | 0 | 3 | 0 | 1 | 2 | 2 | 3 | 3 | 2 |
| Meat and Alternatives 150 | 150 | 17 | 0 | 10 | 0 | 1 | 1 | 1 | 1 | 1 | 2 |
| Fat 50 | 50 | 0 | 0 | 6 | 0 | 3 | 4 | 4 | 5 | 6 | 7 |
| Flavour Enhancer 25 | 25 | 0 | 5 | 0 | 0 | 2 | 2 | 2 | 2 | 2 | 2 |
| Luxury 50 | 50 | 0 | 1 | 5 | 0 | 1 | 1 | 1 | 1 | 1 | 1 |
| Total Calories | | | | | | 1210 | 1410 | 1610 | 1810 | 2010 | 2210 |
| Total grams protein | | | | | | 69 | 87 | 93 | 111 | 115 | 118 |
| Total calories protein | | | | | | 276 | 348 | 372 | 444 | 460 | 472 |
| % of calories from protein | | | | | | 22.81% | 24.68% | 23.11% | 24.53% | 22.89% | 21.36% |
| Total grams carb | | | | | | 145 | 156 | 186 | 197 | 226 | 247 |
| Total calories carb | | | | | | 580 | 624 | 744 | 788 | 904 | 988 |
| % of calories from carb | | | | | | 47.93% | 44.26% | 46.21% | 43.54% | 44.98% | 44.71% |
| Total grams fat | | | | | | 42.5 | 51.5 | 57 | 66 | 73.5 | 86.5 |
| Total calories fat | | | | | | 382.5 | 463.5 | 513 | 594 | 661.5 | 778.5 |
| % of calories from fat | | | | | | 31.61% | 32.87% | 31.86% | 32.82% | 32.91% | 35.23% |
| Total grams fiber | | | | | | 21 | 23 | 25.5 | 27.5 | 31.5 | 34 |
| g fiber 1000 cal | | | | | | 17.36 | 16.31 | 15.84 | 15.19 | 15.67 | 15.38 |

Fiber requirements based on 14 g fiber per 1000 calories
AI for Fiber based on a weight maintenance calorie level is 25 g/day for women and 38 g/day for men

| Macronutrient Distribution Ranges Are "Acceptable" for Each program | | | | | | | |
|---|---|---|---|---|---|---|---|
| | Acceptable | 1200 | 1400 | 1600 | 1800 | 2000 | 2200 |
| Carbohydrate | 45-65% | 47.9% | 44.3% | 46.2% | 43.5% | 45.0% | 44.7% |
| Protein | 10-35% | 22.8% | 24.7% | 23.1% | 24.5% | 22.9% | 21.4% |
| Fat | 20-35% | 31.6% | 32.9% | 31.9% | 32.8% | 32.9% | 35.2% |
| | | 102% | 102% | 101% | 101% | 101% | 101% |
| Fiber (g/1000 Cal) | 14 g/1000 Cal | 17.36 | 16.31 | 15.84 | 15.19 | 15.67 | 15.38 |

TABLE 2

| | | | | | | 1200 cal | 1400 cal | 1600 cal | 1800 cal | 2000 cal | 2200 cal |
|---|---|---|---|---|---|---|---|---|---|---|---|
| | Cals | Protein | Carbs | Fat | Fiber | | | | | | |

Example Food Guide

Balanced-45% Carbohydrate, 25% Protein, 30% Fat

| | Cals | Protein | Carbs | Fat | Fiber | 1200 cal | 1400 cal | 1600 cal | 1800 cal | 2000 cal | 2200 cal |
|---|---|---|---|---|---|---|---|---|---|---|---|
| | | | | | | Recommended number of servings/day | | | | | |
| Free Vegetables 10 | 10 | 1 | 3 | 0 | 1.5 | 6 | 6 | 6 | 6 | 6 | 6 |
| Sweet Vegetables 50 | 50 | 2 | 10 | 0 | 2 | 1 | 1 | 1 | 0 | 0 | 0 |
| Starchy Vegetables 100 | 100 | 3 | 21 | 0 | 2.5 | 0 | 0 | 0 | 1 | 1 | 2 |
| Fruit 50 | 50 | 1 | 11 | 0 | 2 | 1 | 2 | 3 | 5 | 5 | 6 |
| Whole Grains | 100 | 3 | 18 | 1..5 | 2 | 3 | 4 | 4 | 4 | 5 | 5 |
| Milk and Alternatives 100 | 100 | 8 | 15 | 1 | 0 | 2 | 2 | 2 | 1 | 1 | 2 |
| Milk and Alternatives 150 | 150 | 10 | 16 | 5 | 0 | 0 | 0 | 0 | 1 | 1 | 1 |
| Meat and Alternatives 100 | 100 | 17 | 0 | 3 | 0 | 2 | 2 | 2 | 3 | 3 | 2 |
| Meat and Alternatives 150 | 150 | 17 | 0 | 10 | 0 | 1 | 1 | 2 | 2 | 2 | 2 |
| Fat 50 | 50 | 0 | 0 | 6 | 0 | 2 | 3 | 3 | 3 | 5 | 7 |
| Flavour Enhancer 25 | 25 | 0 | 5 | 0 | 0 | 2 | 2 | 2 | 2 | 2 | 2 |
| Luxury 50 | 50 | 0 | 1 | 5 | 0 | 1 | 1 | 1 | 1 | 1 | 1 |
| Total Calories | | | | | | 1210 | 1410 | 1610 | 1810 | 2010 | 2210 |
| Total grams protein | | | | | | 85 | 89 | 107 | 112 | 115 | 124 |
| Total calories protein | | | | | | 340 | 356 | 428 | 448 | 460 | 496 |
| % of calories from protein | | | | | | 28.10% | 25.25% | 26.58% | 24.57% | 22.89% | 22.44% |
| Total grams carb | | | | | | 134 | 163 | 174 | 208 | 226 | 252 |
| Total calories carb | | | | | | 536 | 652 | 696 | 832 | 904 | 1008 |
| % of calories from carb | | | | | | 44.30% | 46.24% | 43.23% | 45.97% | 44.98% | 45.61% |
| Total grams fat | | | | | | 39.5 | 47 | 57 | 61 | 74.5 | 81.5 |
| Total calories fat | | | | | | 355.5 | 423 | 513 | 549 | 670.5 | 733.5 |
| % of calories from fat | | | | | | 29.38% | 30.00% | 31.86% | 30.33% | 33.36% | 33.19% |

TABLE 2-continued

Example Food Guide

| | | | | | | |
|---|---|---|---|---|---|---|
| Total grams fiber | | 19 | 23 | 25 | 29.5 | 31.5 | 33.5 |
| g fiber 1000 cal | | 15.70 | 16.31 | 31.86% | 30.33% | 33.36% | 33.19% |

Fiber requirements based on 14 g fiber per 1000 calories
A1 for Fiber based on a weight maintenance calorie level is 25 g/day for women and 38 g/day for men Macronutrient Distribution Ranges Are "Acceptable" for Each program

| | Acceptable | 1200 | 1400 | 1600 | 1800 | 2000 | 2200 |
|---|---|---|---|---|---|---|---|
| Carbohydrate | 45-65% | 44% | 46% | 43% | 46% | 45% | 46% |
| Protein | 10-35% | 28% | 25% | 27% | 24% | 23% | 22% |
| Fat | 20-35% | 29% | 30% | 32% | 30% | 33% | 33% |
| | | 102% | 101% | 102% | 101% | 101% | 101% |
| Fiber (g/1000 Cal) | 14 g/1000 Cal | 15.70 | 16.31 | 15.53 | 16.30 | 15.67 | 15.16 |

Figure 5D:
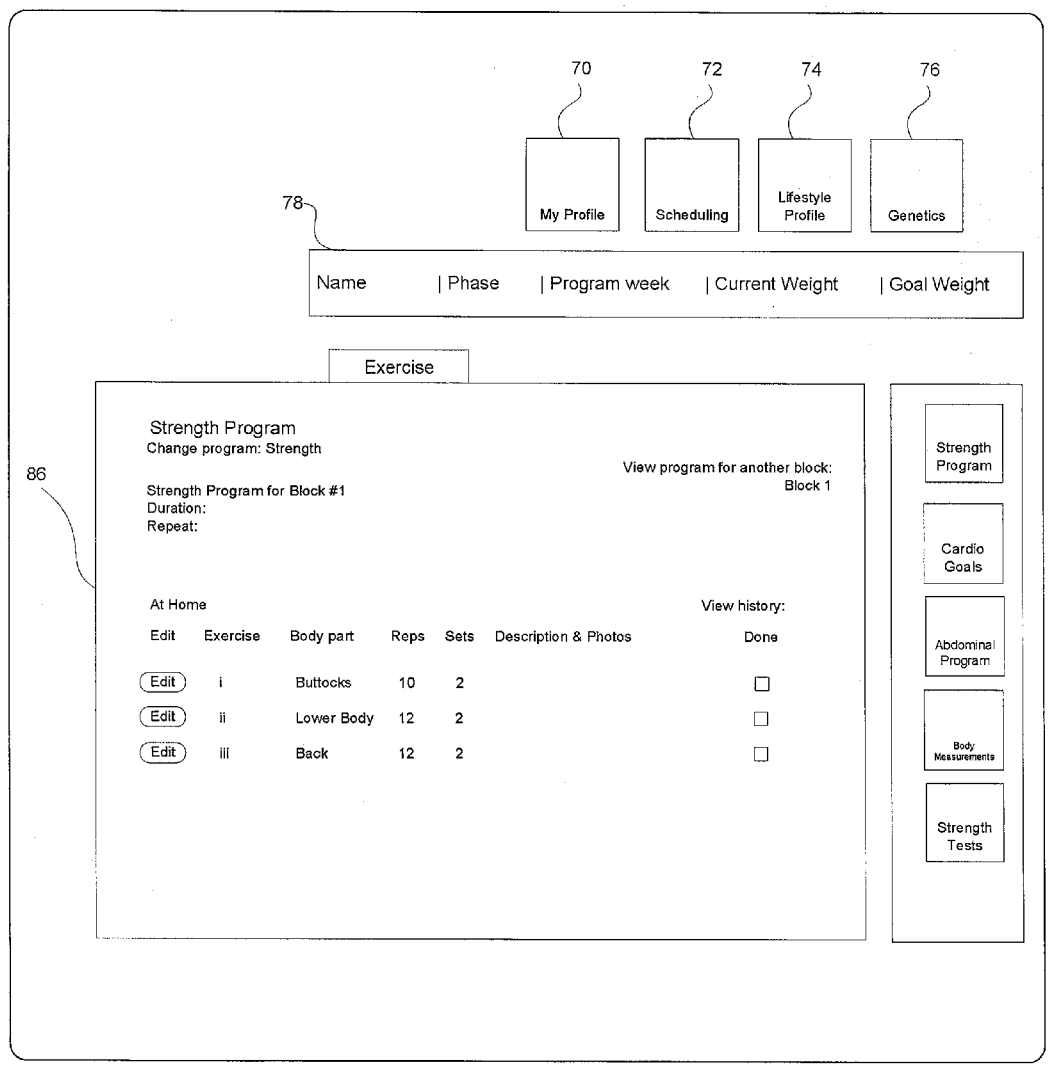

FIG. 5d illustrates an exercise portal (86). The exercise portal may include web pages corresponding to a strength program, cardio goals, abdominal program, stretching program, body measurements, strength test, etc. For example, the strength program web page may include a table that, for each exercise block, a breakdown of the exercises to be completed by the individual. The rows of the table, for example, list the exercise (e.g. i, ii, iii), the body part the exercise targets (e.g. buttocks, lower body, back), and the number of repetitions (reps) and sets to complete. The individual may complete the exercises and complete the table accordingly, for example by selecting a "done" control which signifies that the sets and reps have been completed for the exercise. The individual may also enter notes/descriptions as well as photos for additional tracking.

Figure 5E:
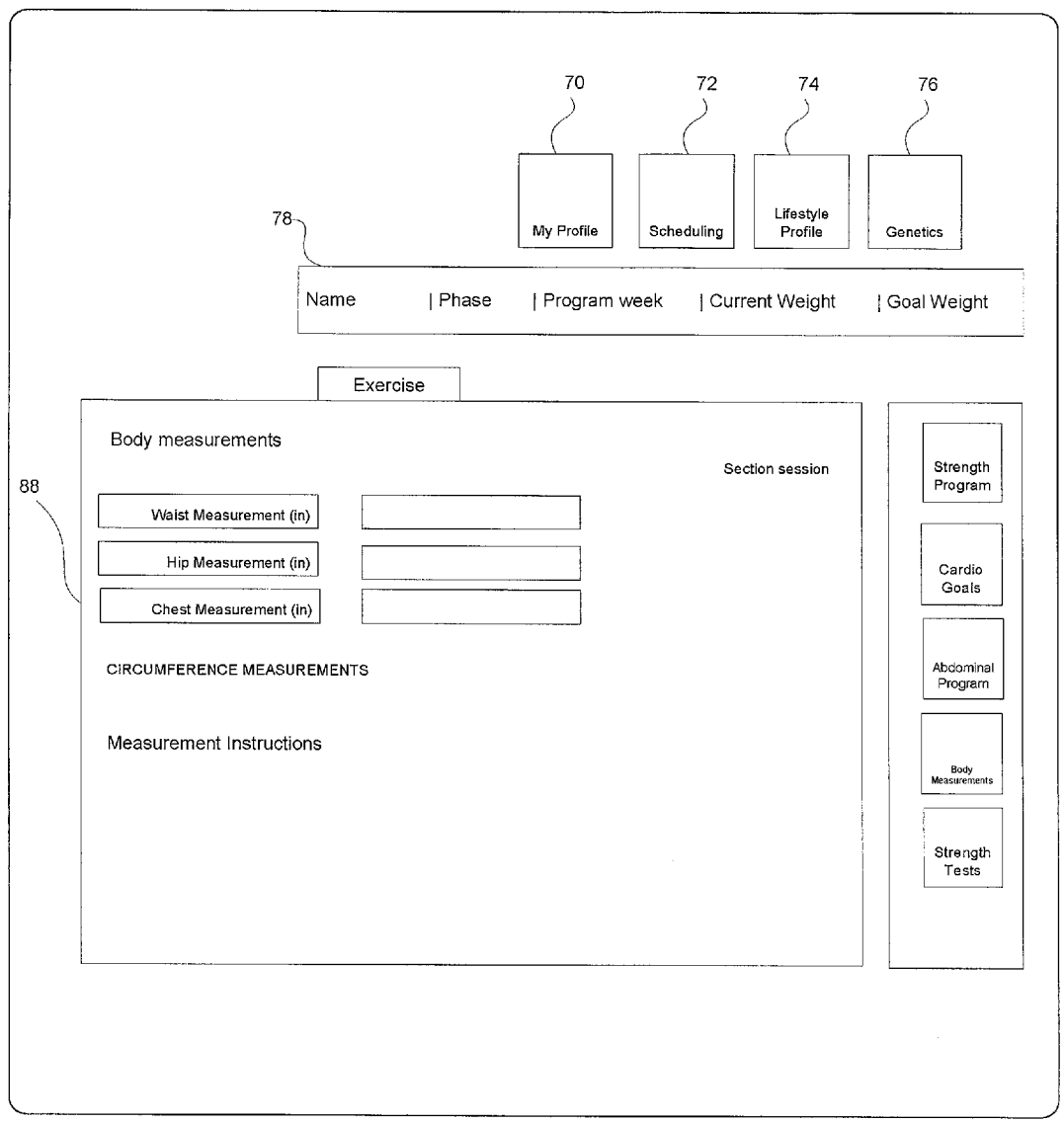

FIG. 5e illustrates the body measurements web page (88). The individual may enter their measurements and be given instructions on how to correctly and accurately perform the measurements.

Figure 5F:
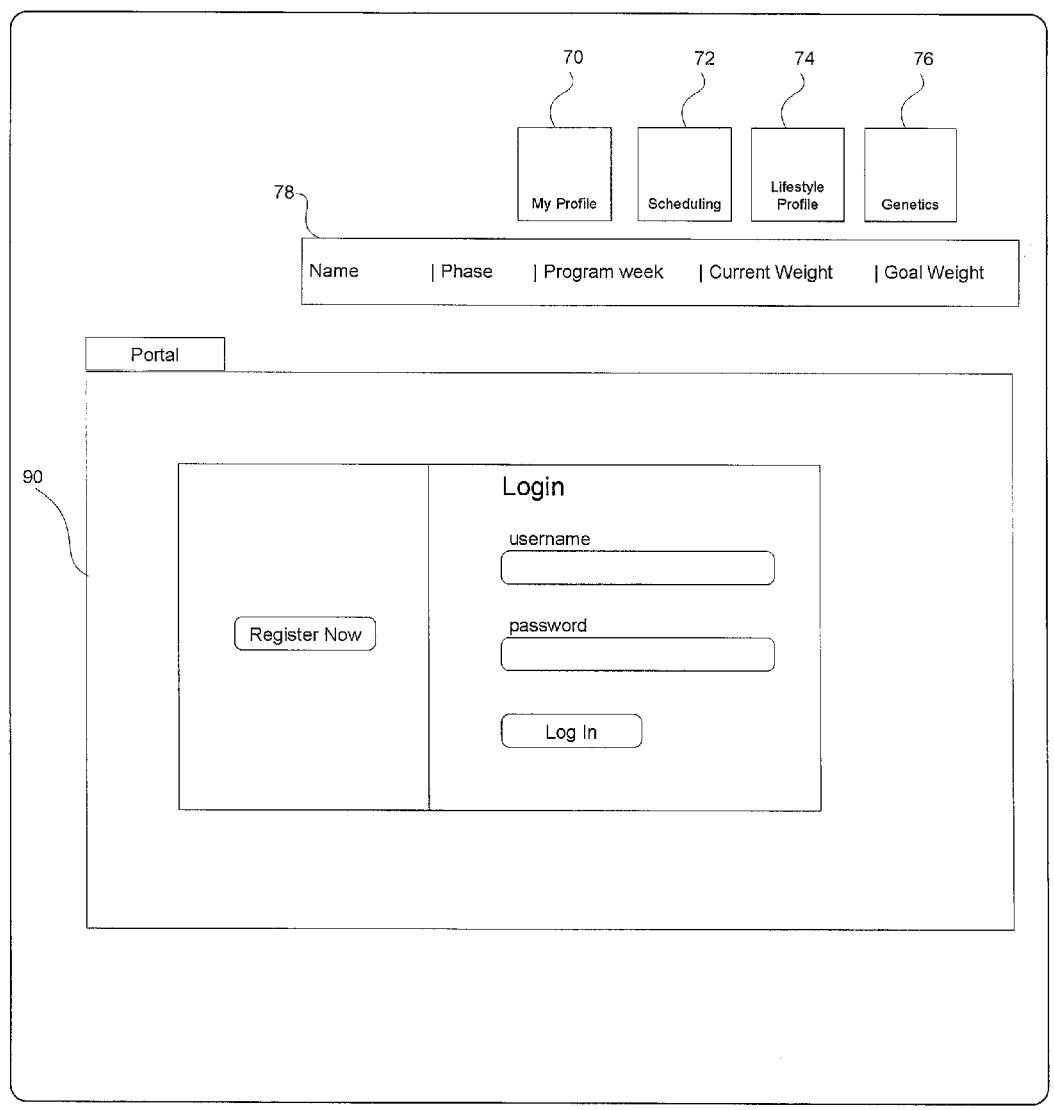

FIG. 5f illustrates an authentication portal (90) for logging in to the system. The portal may include a registration control and a login control, including username and password inputs for the individual to authenticate to the system.

Figure 6:
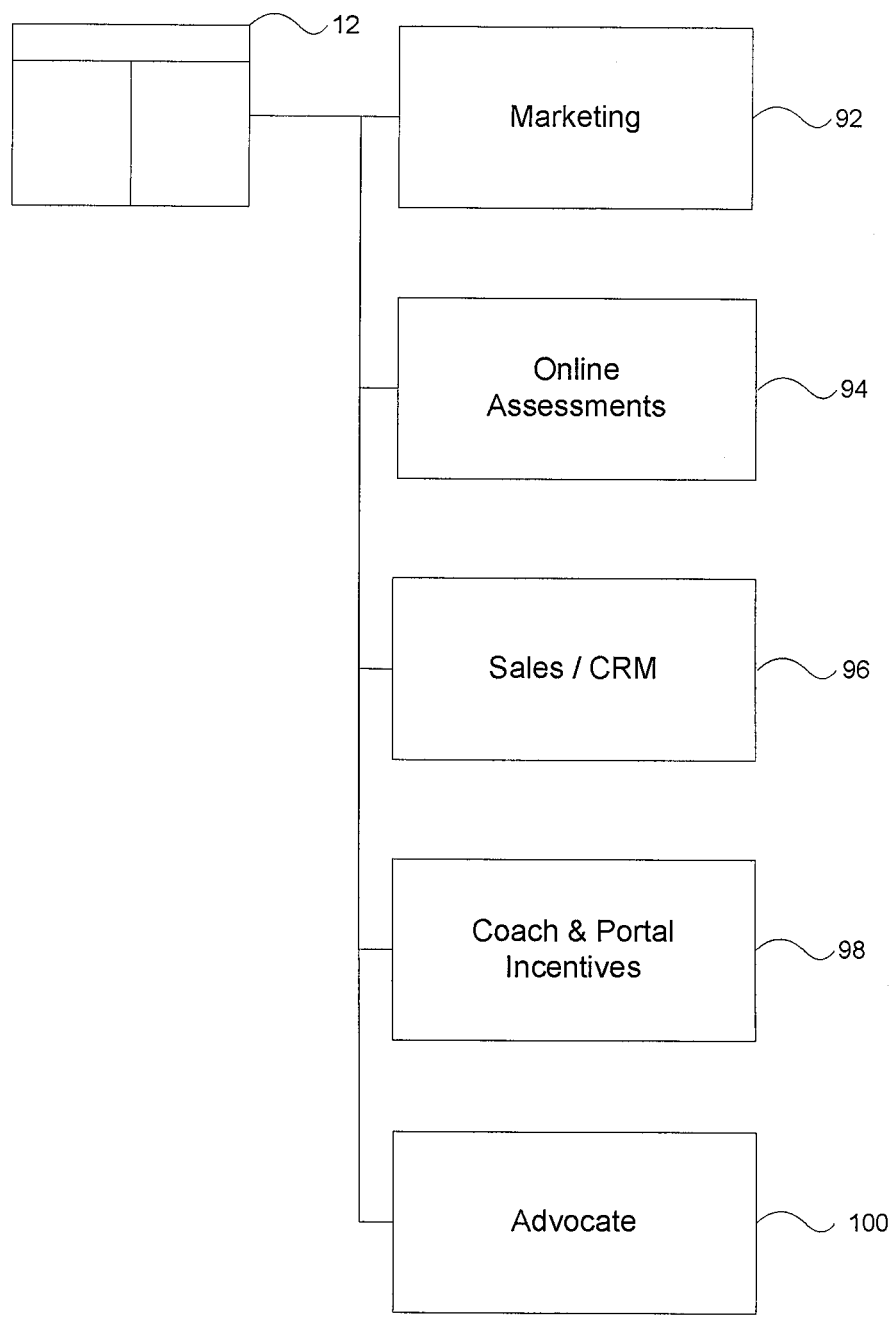
FIG. 6 illustrates the integrated disease and lifestyle management provided by the present invention.

FIG. 6 illustrates the integrated disease and lifestyle management provided by the present invention. This aspect of the invention is further explained below.

It should be understood that one of the advantages of the present invention is that the capture utility (28) and template utility (30) can be updated from time to time to reflect the latest science on disease management by including new information parameters affecting disease management and also strategies for eliciting specific behaviour modification results related to disease management.

It should be noted that the capture utility (28) is operable to obtain information from clients, that is then used to establish optimal program template selection for them. The capture utility (28) is also regularly triggered, for example based on the program template selected for an individual client, in order to obtain more up to date information to track progress of the individual. This information is also stored to the database (10) in order to provide access to selected information, or analysis of information by operation of the analysis engine, to coaches for example via the coaching platform (24). In other words, one of the functions of the system of the present invention is to track the progress of multiple clients relative to their selected program templates.

The application server (12) also includes an analysis engine (32). It should be understood that the analysis engine (32) may include or be linked to analytics functionality that is operable to analyze data in the database for example to generate reports regarding progress of groups of individuals (based for example on common demographic, lifestyle, disease, their coach assignment or other criteria). These reports may be used for example to assess effectiveness of program templates, coaches, coach matches, or other aspects of operation of the present invention.

It also should be understood that the analytics functionality may enable automatic adjustments to selections of program templates, coaches, frequency or nature of coaching interaction or other communications or other system parameters.

The application server (12) also includes an information utility (34) that is operable to store to the database selected information (whether in document, video, audio, audio/video, POWERPOINT™ presentation etc.) regarding various disease management related topics, such as nutrition as just one example. The information utility (34) is operable (for example in co-operation with the analysis engine (32)) to present to a user, based on their individual attributes for example or their program template defined by the system, specific information. Information may be selected for example based on such factors as content or style of writing based on behaviour attributes, real time progress of individual clients relative to their program template.

The categorizations and behavioural attributes discussed above may be automatically determined by the analysis engine (32) (which incorporates one or more analytical tools), based on information obtained from the client, for example by operation of the capture utility (28). As stated before, the individual classifications may be based on a combination of a plurality of categorizations of the individual based on their individual attributes. In yet another aspect of the invention, the categorizations include one or more of nutrition categorizations (caloric intake), exercise intensity categorizations (e.g. beginner, intermediate, advanced), exercise location categorizations (home-based or gym-based), and behavioural attributes relative to nutrition, fitness, and/or weight management (e.g. "Emotional", "Disconnected", "All or None"). The permutation of the categorizations defines a set of individual classifications, which determine the selection of an effective program template by operation of the analysis engine (32), relying on the templates stored to the database (10) by operation of the template utility (30).

For example, the capture utility (28) may be accessed by a web page interface that provides an individual with a plurality of questions to determine nutrition, fitness and behaviour attributes. For example, fitness questions may include asking the individual to identify whether they are generally: (i) sedentary (e.g. up to 3.75 hours per week of moderate activity), (ii) low active (e.g. at least 3.5 hours and up to 6.75 hours per week of moderate activity), (iii) active (e.g. at least 7 hours and up to 20.75 hours per week of moderate activity equivalents), or (iv) very active (e.g. at least 21 hours per week of moderate activity equivalents).

Other example fitness questions and answers are shown below in Table 3.

TABLE 3

Sample questions and answers

| Questions | Possible Answers | Individual's Answer |
|---|---|---|
| On each day of the week, are you on your feet moving around for at least 1.5 hours a day? This can include household chores, walking to and from your house, shopping, tasks at work, etc. | 1. No<br>2. Yes<br>3. Yes and my work is physically active with walking and lifting at least 4 hours per day on at least 4 days per week. Examples include nursing, hotel housekeeping, landscaping, construction work, fire fighting. | 3 |
| In a typical week how often do you engage in VIGOROUS ACTIVITY (days/week)? | a. 0<br>b. 1 to 2<br>c. 3 to 4<br>d. 5 to 7 | d |
| How long does your vigourous activity last? | a. less than 15 minutes<br>b. 16 to 30 minutes<br>c. 31 to 45 minutes<br>d. 46 to 60 minutes<br>e. greater than 60 minutes | d |
| In a typical week, how often do you engage in MODERATE ACTIVITY? (days/week) | a. 0<br>b. 1 to 2<br>c. 3 to 4<br>d. 5 to 7 | d |
| How long does your moderate activity last? | a. less than 15 minutes<br>b. 16 to 30 minutes<br>c. 31 to 45 minutes<br>d. 46 to 60 minutes<br>e. 61 to 120 minutes<br>e. greater than 120 minutes | b |

The analysis engine (32) analyses the provided information to calculate scores that are translatable to categorizations, as described above.

The capture utility may also include questions relating to the individual's demographic information (e.g. gender and age). The age range specified may result, by means of the analysis engine, in an age range that may be determined hosen based on generalizations regarding health needs of persons in the particular age range. For example, a woman between 18-40 years of age may require some extra help to stay on track with their health while a woman between 41-60 years of age may be experiencing some turbulent hormonal changes. Thus, defining as two age ranges, 18-40 and 41-60 may be optimal. The capture utility may also request the individual specify the reasons for seeking weight loss or nutritional improvement, for example so as to improve health, appearance, to feel better, for a particular event, to lose weight after pregnancy, to become more physically fit, to alleviate health concerns, etc.

The age ranges could also be chosen based on common behavioural characteristics. For example, women between 18-40 years of age are often building the foundation of their life goals for work, family and relationships. They may be experimenting with different work-life balances to see how they fit. It is an exciting and busy time of life. Many women gain weight in early adulthood. Life is so busy and interesting that eight hours a night of sleep may be sacrificed. Inadequate sleep may affect their hormones so they are more likely to store fat and crave carbohydrates. This is also the age of prime reproductive fertility with monthly cycles of hormonal changes that affect more than just ovulation. There may be specific days of their cycle when they are much more vulnerable to cravings, overeating, uncomfortable emotions, lower energy and less motivation to exercise. They may be looking for some extra help to stay on track with their life goals on these days.

Correspondingly, women between 41-60 years of age may be approaching peri-menopause and menopause; their lives may be turbulent and powerful. They may believe that everything around them is changing in unpredictable ways while they feel a strong sense of who they are and what they are truly meant to do with their lives, experiences, knowledge, skills and talents. Their years of life experience make them efficient, intuitively on target and productive in activities. While they are feeling personally powerful they may be experiencing some physical signs of aging and hormonal changes. Fat cells may be migrating from legs to midriff creating an unwelcomed "spare tire". Energy and sleep quality may have changed and they feel fatigued, especially if they experience hot flashes at night. Their mood may be depressed, anxious or sometimes irritable. Their skin may be getting dry or they may be losing hair. They may have digestive problems, such as gas or bloating. Their libido may be decreased. They may be gaining weight. Thus some lifestyle changes and targeted abdominal exercises may help boost metabolism, improve mood and energy, reverse weight gain and flatten their belly. Overcoming age-related body changes will give them an even stronger sense of self and strengths.

Further age ranges may also be defined for men and women.

Further questions may relate to whether the individual is a smoker, work-a-holic, heavy drinker. Questions may also be directed to historical measures, such as their highest weight and lowest weight as an adult; or current measures and targets such as weight, BMI, etc. Questions may be directed to eating habits and allergies.

Additional questions may relate to exercise, for example whether the individual is a member of a fitness center or has plans to join one, or has access to exercise equipment at home. The individual could also be asked questions such as to select statement that best describe their current participation in strength and/or cardiovascular exercise. Possible answers could be preconfigured, such as (1) other than daily living and household chores, I do not participate in any type of strength activities; (2) I currently lift weights 1 to 2 days a week; or (3) I currently lift weights 3 days a week or more.

The capture utility may also be used to determine contraindications to the program, such as exercise contraindications. For example, the individual may be asked: (1) Has your doctor ever said that you have a heart condition and that you should only do physical activity recommended by a doctor?; (2) Do you feel pain in your chest when you do physical activity? (3) In the past month, have you experienced chest pain when you were not doing physical activity? (4) Do you lose your balance because of dizziness or do you ever lose consciousness? (5) Do you have a bone or joint problem (for example, back, knee or hip) that could be made worse by a change in your physical activity? (6) Is your doctor currently prescribing drugs (for example, water pills) for your blood pressure or heart condition? (7) Do you know of any other reason why you should not do physical activity?

If the individual answers "no" to all the contraindications, the web interface may display a message indicating the individual is suited to begin the program. Otherwise, a warning message may be displayed, encouraging the individual to seek medical advice.

Genetic questions may also be asked, including relating to family histories of disease such as obesity (and whether the family history relates to father, mother, brother, sister, etc.). Based on whether the individual indicates any or significant family history of the illness, the web interface may display a message to the individual recommending that the individual undergo a genetic test to determine whether the individual is predisposed to have the illness.

Question may also be asked about the medications an individual is taking and the illnesses they suffer from. Other illnesses, health issues, or medical needs that could be asked include fatigue, menopause, premenstual syndrome, menstrual cramps, hormone imbalances, elevated hormone levels, vitamin deficiencies, anxiety, birth control related, memory, depression, cancer, heart disease, atherosclerosis, coronary artery disease, bone fracture prevention, high triglycerides, blood pressure, cholesterol, rheumatoid arthritis, seasonal affective disorder, constipation, indigestion, asthma, diabetes, multiple sclerosis, prostate health related, acne, diarrhea, impotence, erectile dysfunction, exercise fatigue, stress, food craving, appetite control, hypothyroidism, iron deficiency, anemia, osteoarthritis, knee osteoarthritis, lower back osteoarthritis, weight gain, excess boy fat, slow metabolism, etc. For each illness or medical needs specified, the web interface may be configured to recommend to the individual one or more nutritional supplements to help treat the condition.

The capture utility (28) may also provide the individual with a plurality of questions to determine behaviour attributes. For example, behaviour questions may be multiple choice with possible answers including (i) never; (ii) rarely; (iii) sometimes; (iv) often; and (v) always. Questions may include, to determine subtype A, emotion based: (i) How often do you (over)eat in response to negative emotions like anxiety, anger, loneliness or boredom?; (ii) How often do you (over)eat in response to stress or feeling overwhelmed with the demands of work and/or home?; (iii) How often to you (over)eat when you have had a bad day, or experienced negative interactions with others (family, spouse, coworkers, etc.)?; (iv) How often do you eat when you are avoiding or putting off doing something you know you should do?; (v) How often do you have trouble controlling your eating when you have positive feelings (e.g., overeating to celebrate a special event or accomplishment)?; (vi) How often do you "under-eat" or eat less in response to negative events/stressors, and/or experience physical symptoms of stress (e.g., nausea, upset stomach, feeling keyed up) that make it difficult to eat properly?.

Questions may also include, to determine subtype B, disconnectedness: (i) How often do you find yourself eating/snacking even though you are not physically hungry?; (ii) How often do you have trouble controlling your eating when your favourite foods are in the house? (iii) How often have you eaten a large amount of food in a short period of time (i.e., binge-eating) and felt afterwards that your eating was out of control?; (iv) How often do you eat or drink too quickly?; (v) How often do you eat standing up or watching TV?; (vi) If you see a tempting food you know you really shouldn't eat, how often do you think It's OK" to eat this food because "I'll make up for it later" or "No one is watching" or "I can start again tomorrow"?.

Questions may also include, to determine subtype C, emotion based (i) How often do you find it hard to stay motivated to follow a diet and/or exercise plan for the time it takes to reach your goal?; (ii) When dieting, how often do you find you are resistant to changing your eating and/or exercise habits?; (iii) How often do you get discouraged when dieting?; (iv) How often do you feel that eating well/exercising regularly is just too much work or is just too hard?; (v) How often do you find it hard to resist certain foods when you are out with friends/at a restaurant/work or family function?; (vi) How often do you eat something you know you shouldn't because you think "People will be offended if I don't eat it", "Everyone else is eating it" or "People will comment that I'm eating differently from them"?

It should be understood that during of after collection of the individual's information by the capture utility, the capture utility may trigger the web interface to display encouraging or motivational feedback based on the individual's responses. For example, if an individual is already active, the capture utility may trigger the web interface to display a congratulatory message to the individual. If the individual is not active, the web interface could display a warning message regarding the long term consequences of such a lifestyle. The capture utility may also trigger the web interface to display health information regarding the individual's nutritional feedback. For example, if the individual specifies that they eat out of boredom, the web interface could display to the individual possible reasons for such a behaviour.

The analysis engine (32) may assign an average score of the individual's responses for each subtype. For example, "never" may be assigned 0, "rarely" 1, "sometimes" 2, "often" 3 and "always" 4. The analysis engine (32) may classify the individual's subtype based on the highest average subtype score. In case of a type, the subtype may be classified as "false" and/or the subtype may be determined by narrowing the number of questions to calculate the average. For example, the three highest scoring questions of the subtypes may be averages to determine the subtype.

It should be noted that more or different categorizations or behavioural attributes may be utilized.

As illustrated in FIG. 6, in accordance with the present invention a number of features are integrated in the operation of the invention, through integration into the application server of a number of functions that rely on features such as for example the behavioural attributes. FIG. 6 shows for example that online assessment (94) (through the capture utility (28) for example), sales/marketing processes (92) (and associated functions or utilities of the application server (12) that are sales/marketing related, such as for example incorporation of a customer relationship management (CRM) utility (96), and coaching/incentives (98) (by operation of the coaching platform (24)) are integrated to provide a set of communications and interactions facilitated by the system, directed to clients, directed to coaches to guide coaching of clients, or directed to client/coach interactions.

The behavioural attributes may be relied upon by the system to automatically direct the sales/marketing activities, coaching approach, presentation of program, or presentation of information to the particular client.

For example, an example of the basis on which the system is operable to automatically determine sales/marketing, coaching or presentation directions to sales/marketing staff or coaches for example, based on the behavioural attributes is given below in Table 4.

TABLE 4

Coaching or presentation directions based on behavioural attributes.

|  | Emotion based | Disconnected | All or None |
| --- | --- | --- | --- |
| Sales/ Marketing | Appeal to client's emotions since are motivated by how they feel "in the moment". Emotional eaters are thought to be more impulsive, primed to act in relation to external cues. Initial visit/assessment should be fun, positive, encouraging; program should feel accessible; summary of assessment should be compelling/call to action. Impression of program/coaches should be one of order, calm. Focus on the 5 senses of the experience: smells, lighting, colours, order; office should be inviting/welcoming, warm. Emphasize the association of how good it feels to be healthy, balanced and fit; the allure of living life according to the program. Appeal to sense of belonging, "that membership has its privileges". Program offers an individualized approach that focuses | Appeal to need for immediate gratification since client finds it hard to slow down, or delay pleasure, these clients yearn for positive experience/stimulation. Work to develop good rapport, positive feel in office at first visit. First impressions are very important for these clients. Should walk out of initial assessment with something tangible (e.g., the "NT SWAG bag") so experience was gratifying and leaves a good impression. Need clarity and simplicity in delivery of the message/sales pitch. "Bottom line" type of people, may not pay attention to the smaller details. Advertising needs to be compelling, appeal to them at first glance; so can get the "take home" message quickly. Assessment summary should also be brief, to the point, easily understood and compelling. These clients may not tend to be as methodical or thoughtful in their decision making, and make quick judgments | Appeal to their desire for results, need for support/helping hand to keep them on track. Important to really motivate these people, educate them about how the program is different than other programs they may have tried. In the past since may be more jaded or reluctant to "buy in", especially highlight the differentiating factors like genetics or well-being. Previous failures may not have been their fault, using the power of genetics and psychology to create a blueprint for enhanced success May be more sceptical initially, have to find a personal "hook". What motivates them about being fit, healthy, losing weight? These clients generally know they have a hard time with diets, weight loss plans. Important to be empathic to their past struggle and to their potential scepticism about our claims. Important to "instil hope" in client and faith in the components of the program from beginning. At early stages, motivated by testimonials and new aspects of program like genetics Important to highlight these components in advertising, sales pitch. |

TABLE 4-continued

Coaching or presentation directions based on behavioural attributes.

| | Emotion based | Disconnected | All or None |
|---|---|---|---|
| | on your main issues/stressors and how to manage these to achieve success in weight loss. Value in testimonials, hearing about others with similar insecurities, pressures/stresses/busy lives that have succeeded. | based on their "gut feeling" or desire for results or belonging. Best opportunity to sign them up is at the moment when in the office for first time, may not be as likely to return if not signed at first contact. | |
| Motivation/ Role of Coach | May have lower self-esteem, public self-consciousness, concern about what others think-fear of being judged. So coaches need to be non-threatening, relatable, welcoming, like regular people, not super-fit/supermodels, but approachable, friendly. Be more open to sharing personal experiences. Importance of being empathic, listening in a non-judgmental fashion. Women of this subtype in particular may tend to put needs of others first (e.g. family etc.) and neglect their own needs. So coaches need to emphasize how they can be better for family when they feel better about themselves, can manage stress/eating/weight issues with greater confidence. Emphasize link between busy stressful lives and how it can interfere with successful weight loss. Important to target in a weight program for best success. The program can increase their sense of control. It will take the guesswork out of losing weight and provide a formula that is proven and guided by your own coach. | Present a clear rationale for the program and each component. If client makes a quick judgment, they may be more likely to have "buyers remorse", feel guilty or second guess their decision to join the program. Important to be prepared for this type of reaction, to determine best ways to follow up at first visit, set up system of appointments/best way to contact etc., at first few visits. Help them to remain positive about their decision, demonstrate how the coach/program will be helpful etc. May end up revisiting many of the same details from the initial session in a clear fashion at the second visit. Be prepared for more questions, doubts or scepticism about program at subsequent visits. Beyond the initial decision, which may be quick and impulsive for some of these clients, need to work to keep them engaged and hooked on program and positive experience of being in the program. | Clients may either be resistant to the idea of committing to "one more program" or be chomping at the bit to start, but then may lose this drive once confronted with a setback or if feel overwhelmed. Clients may be more jaded, edgy, sarcastic, demanding and take more of the coach's energy. May be best when possible to schedule them at your higher energy times, and not back to back. Try to leave time to debrief with other coach before or after these clients. Role of continuing to balance hope for them, to keep them motivated, that you believe in their efforts and congratulate them on successes along the way. May be more likely to disqualify small successes, important to highlight success and get them to pay attention to weekly milestones (not just emphasis on weight). Coach having attitude of "being in it with them". Collaborative stance, being empathic about how hard weight loss can be; that are there to help figure things out with them along the way to ensure success. Clients may be fired up, highly motivated in early stages and then lose momentum. Important to develop alliance with coach so can provide well-timed encouragement. Make a plan ahead of time of best ways to contact. Let them know there may be tough times/plateaus, but are committed to helping them work through the tough times. Emphasis on creative problem solving during "stuck" times. Importance of regular contact to keep momentum, positive feeling/alliance going, even if have to do phone sessions some weeks etc. |

TABLE 4-continued

Coaching or presentation directions based on behavioural attributes.

| | Emotion based | Disconnected | All or None |
|---|---|---|---|
| Program Presentation | Sessions should be fun and interesting, but with a clearly defined purpose so seems worthwhile given busy schedules. Can't feel like it is creating more stress. Don't want to overwhelm them with too many details/work in first few sessions. Let them "warm up" to program, importance of planning exercises, how program will fit this into their lifestyle. Possible supplements include stress/mood support. | Order of exercises should add value in early session and be clearly presented. Clients may want to rush sessions, but make sure they understand key principles of exercises at each session. Provide quick summaries etc. | Feed components of program to them more gradually so as not to overwhelm or de-motivate (especially with nutrition, which has a heavier content base). Even if feeling very motivated and excited at the start, if too much is presented, they may go home and feel overwhelmed, or fail at implementing the exercises. Feed techniques as building blocks with clear rationale. Lay foundation for success at early stages. Start with aspects where they can see an "early gain", for example supplements. They will start to feel better, more energy, some water loss etc.. Introduce wellbeing exercises with planning emphasis, how it will fit in the different parts like nutrition, exercise etc. Make a "real plan" that is manageable, achievable and measurable. |

The coaching platform (24) is best understood as a set of utilities or tools that enable interaction between coaches and clients as described in the present invention. The coaching platform is similar to a CRM utility that implements coaching interactions, as directed by the system based on for example the behavioural attributes and the program templates, and progress of clients relative to the program templates. The user cases set out below help to understand the operation of the coaching platform (24).

Wireless Implementation

It should be understood that the communication server (14), and other aspects of the present invention, may be implemented and configured such that interaction between clients and the system, and also interactions between coaches and clients by operation of the system, can occur via wireless devices. For example, the communication server (14) may include one or more wireless modules that enable communications described herein to be pushed to wireless devices associated with clients and/or coaches. A wireless device client may be provided for loading on the wireless device to enhance the ability of users to interact with the system of the present invention via a wireless device such as a smart phone.

Social Networking

It should be understood that the web server (16) may define additional web pages (18) that enable clients to interact with one another, for example to share information, testimonials, provide encouragement, communicate for the purposes of setting up exercise groups, support groups etc. In one aspect of social networking interactions enabled by the present inventions groups of clients may compete with one another to achieve goals, for example goals set for clients based on their program template. In one aspect of the system of the present invention, the web server (16) incorporates a social networking module that enables clients to create and populate social networking web pages, and link these with "friends" and communicate with groups of friends via the social networking module. The present invention contemplates the system directing social networking processes in the sense of automatically suggesting clients that share common attributes with other clients, for example, common behavioural attributes, common program templates or shared stage in execution of a program template, common challenges in adherence to a shared program template etc. The invention contemplates the social networking module incorporating the various functions, features and resources associated with social networking that exist or may be developed in the future.

E-Commerce

In another aspect of the system, the web server (16) is linked to an e-commerce server that enables clients to order and pay for specific products such as nutritional supplements, exercise equipment or clothing, ingredients to make recipes, etc. suggested by the system.

Video Games and Virtual Worlds

The operation of the system of the present invention can be extended by developing and distributing video games or virtual worlds that are used as part of program templates (for example using Wii™ type games as a means of encouraging exercise). Virtual worlds can also be used as a means of promoting interactions between clients or between clients and their coaches.

Tracking Hardware

In another aspect of the present invention, activities of clients may be tracked by a device in real time for example via behavioural data collected using a mobile device or a "pedometer" carried by the client. This enables the collection of exercise habits for example of specific clients, which can then be provided via the communication server (14) to the capture utility (28) for tracking. Tracking may be provided in real-time to enable making program changes adaptively.

Genetic Testing

In another aspect of the invention, the individual attributes also relate to nutrition and/or fitness related genetic markers for an individual, established using one or more genetic tests, to produce genetic tests results for the individual. The genetic tests may relate to testing for the FTO gene, the MC4R gene, and/or the DRD2 gene. The genetic test results may be used as further individual attributes that in turn define the selection of the program template. Alternatively, the nutrition, fitness and/or weight management program attributes may be further personalized based on the genetic test results, including automatically by providing the genetic test results to the coaching platform.

The relevance of the above identified genes is set out below.

Genetic Susceptibility to Gain Weight: the FTO Gene

The most convincing evidence to date for a gene associated with obesity an increased susceptibility to weight gain has been found for the fat mass and obesity associated (FTO) gene. This obesity gene was identified through a human genome wide search for type 2 diabetes susceptibility genes in a study published in the prestigious journal Science in April 2007 (Frayling et al, 2007 #2). In that study, Frayling and co-workers reported a strong (p value=$10^{-14}$) and robust association between a common variant (T/A) located within the first FTO intron (rs9939609) and body mass index (BMI), a finding which concurred with the results of other independent studies published almost simultaneously (Dina et al, 2007 #4; Scuteri et al, 2007 #6). The 16% of adult subjects who had the AA genotype weighed about 3 kg more and had a 1.67 fold increased odds of obesity compared to the non-carriers (TT genotype). This association was observed from age 7 yr upward and was replicated in 13 cohorts with a total of more than 38,000 subjects (p value=$3.0\times10^{-35}$). The association of the FTO gene with BMI was replicated in several populations of different ethnic origins (Scott, 2007 #3; Chang, 2008 #27; Gonzalez-Sanchez, 2008 #22; Peeters, 2008 #9; Marvelle, 2008 #28; Tan, 2008 #23; Jess, 2008 #25) and the gene was also found to be associated with measures of body fatness, insulin sensitivity, resting metabolic and a reduced capacity of fat cells to break down fat (Scuteri et al, 2007 #6; Do et al, 2008 #11; Wahlen et al, 2008 #8} and with weight gain based on longitudinal data Furthermore, two recent studies suggested that low physical activity level accentuates the effects of the FTO gene on body fatness (Andreasen et al, 2008 #20; Rampersaud et al, 2008 #29).

The function and pathway by which FTO leads to an increase risk of obesity are not known currently, but gene expression studies have shown that FTO is expressed in adipose tissue and regions of the brain involved in the regulation of energy balance (Frayling, 2007 #2; Dina, 2007 #4; Gerken, 2007 #7). A recent study showed that the adipocytes of subjects carrying the FTO at risk allele (the A allele) have a 30% reduced capacity to mobilize fat (decrease lipolytic activity) compared to TT homozygotes (Wahlen, 2008 #8).

The scientific evidence linking the FTO gene to increased risk of obesity represents by far the most consistent and convincing evidence for a single gene variant associated with increased risk of obesity in the general population (Loos, 2008 #30)

Therefore genotyping of FTO rs9939609 polymorphism is used to assess an individual's susceptibility to weight gain and strongly recommend to subjects at risk of being physically active.

Melanocortin-4 Receptor (MC4R) Gene

The melanocortin-4 receptor, which is found in regions of the brain involved in the regulation of appetite, regulates food intake by integrating satiety signal (Adan, 2006 #33). Mice lacking this receptor are characterized by hyperphagia and obesity in response to an increase in the amount of fat in their diet and activation of this receptor results in a reduction of food intake. Because of its role in the regulation of appetite, the MC4R is a major target for the pharmacological treatment of obesity and several academic and industry research groups are trying to identify selective agonist of the MC4R (Nargund, 2006 #34; MacKenzie, 2006 #35).

Several mutations have been identified in the MC4R gene and the gene is currently regarded as the most relevant genetic cause of severe obesity (Hinney, 2006 #36; Tan, 2008 #38). However, two recent genome-wide association studies revealed that the MC4R gene could play a role in the most common forms of obesity. One of this study based 16,876 subjects (Loos, 2008 #31) found that a common variant (rs17782313; T/C minor allele frequency 24%) near the MC4R gene was associated with BMI (p=$2.9\times10^{-6}$), an association that was confirmed in more than 60,000 subjects (p=$2.8\times10^{-15}$). In the second study based on 11,955 individuals, association of another variant (rs12970134) near MC4R was found with waist circumference, BMI and insulin resistance (Chambers, 2008 #37). Finally, it was recently shown the MC4R rs17782313 variant was associated with higher caloric intake, total fat intake and percent of energy derived from fat (Qi, 2008 #32).

Therefore genotyping of the MC4R rs17782313 polymorphism is used, and a low-fat diet is recommended in C/C genotype subjects.

Dopamine D2 Receptor (DRD2) Gene

Dopamine (DA), also known as the pleasure molecule, is the primary chemical messenger of reward in the brain. Dopamine plays a role in a broad range of human behaviours including food-related behaviours (Wang, 2002 #39). Differences in the sensitivity of the dopamine reward pathways has been associated with various behavioural disorders, including compulsive eating (Davis, 2008 #41; Volkow, 2008 #40).

Since the action of DA in the brain is exerted through receptor binding of synaptic DA, genes coding for DA receptors have been considered as candidate genes of obesity-related behaviours. The DRD2 TaqIA polymorphism (rs1800497) has been one of the most extensively investigated gene variant of the dopaminergic system (Noble, 2003 #42) The minor A1 allele of the TaqIA DRD2 polymorphisms, which is associated with a lower density of D2 receptors (Pohjalainen, 1998 #43) and reduced dopamine binding (Thompson, 1997 #44) is more frequent in obese subjects than in lean controls (Noble, 1994 #45). Studies have shown that brain dopamine D2 receptor availability, measured by PET scan, was reduced in obese individuals in proportion to their BMI, which suggests that dopamine deficiency in obese individuals may lead them to overeat as a way to compensate for decrease activation of the dopaminergic reward system (Wang, 2001 #46; Wang, 2004 #47). A very recent study published in Science last October (Stice, 2008 #48) supported that hypothesis by showing, using functional magnetic resonance imaging techniques, that obese individuals carrying the A1 allele had 30% to 40% fewer D2 receptors than A2/A2 individuals. They showed that brain activation in response to food intake and food cues was reduced in obese compare to lean individuals and that this response was significantly stronger in individuals carrying the A1 allele, which may prompt them to overeat to compensate for this hypofunctioning dopamine reward system Thus decreased levels of DRD2 predispose subjects to search for reinforcers which, in the case of obese subjects could be food, and this behaviour is exacerbated in individual with the A1 allele of the DRD2 gene. Therefore DRD2 gene polymorphism is tested and behavioural intervention is undertaken for those at risk, by operation of the system of the present invention.

User Cases

The system, method and computer program of the present invention is referred to herein under the trademark NEWTOPIA™.

User Case #1

Assessment

HK completed the Newtopia program assessment at NEWTOPIA'S website on Mar. 12, 2009. Based on the information entered in her assessment, HK is a 42-year-old woman (date of birth Jan. 2, 1967), married with two children, with a primary concern of weight management. Her current weight and height are 187 lbs and 5'5", respectively, leading to a body mass index (BMI) of 31.7 (obese). She wishes to lose 52 lbs, with a goal weight of 135 lbs (BMI=22.5). Her principal reason for losing weight is to feel better overall. Her assessment also included the following information:

She is a part-time teacher.
Her current lifestyle is that of a workaholic.
She has a family physician, Dr. Koren (Bathurst Medical Clinic).
She is comfortable using a computer.
She wishes to take the Newtopia genetic test for weight and lifestyle management.
She has the following servings per day: vegetables (2), fruits (1), 100% whole grains (3), milk and alternatives (4) and meat and alternatives (3).
On a weekly basis, she eats as follows: fish and seafood (1), meat and alternatives (>7), food grown or raised locally or certified organic (0) and food grown or raised by you or members of your family (0).
She drinks 3 cups of water per day.
She is a smoker.
She drinks alcohol 3 times/week.
She is not currently taking vitamins or supplements.
She does not have any allergies or food intolerances.
She has tried to lose weight in the past through Weight Watchers where she lost 15 lbs.
She is not currently involved in any form of continuous exercise.
She does not belong to a gym.
She has equipment at home for exercise: exercise bike and resistance equipment.
She does not participate in strength activities.
She does not participate in cardio activities.
She answered "no" to all the PAR-Q exercise questions.
She is currently taking the following medications: hypothyroid (synthroid), anti-hypertensive (ramipril and HCT), cholesterol-lowering drugs (atorvastatin) and anti-anxiety (sertraline).
She suffers from hypothyroidism, fatigue, low energy, hormonal imbalances, anxiety, high blood pressure, high cholesterol, food cravings, stress management, iron deficiency anemia, constipation and has a family history of heart disease (wishes heart disease prevention).
Based on her exercise assessment, she is classified as low active.
Based on her well-being assessment, she was classified as having disconnected behaviours with respect to weight management.

Program Review and Educate Phase

Following analysis of HK's answers on the Newtopia program assessment, she was contacted by Newtopia program administrators and scheduled to meet with a sales manager. The sales manager reviewed the Newtopia program assessment with HK, explained the Newtopia program and reviewed any contraindications or cautions with the program. HK immediately enrolled into the Newtopia program. The Newtopia program links its coaches and clients based on behavioural synergy between a coach's personality score and the client's behavioural subtype and interests. HK was assigned a coach with a specialty in working with disconnected behaviour related to weight management. Newtopia coaches modify their coaching practices based on the well-being subtype of the client. For clients with disconnected behaviours, the coaching method is focused on making the client aware of why they are involved in a weight management program and to get them more mindful of their lifestyle choices.

She then began the Educate Phase of the program.

Educate Phase

Her weight was recorded at 187 lbs. Based on her nutritional assessment, her coach recommended a diet of 1,400 basic calories daily. Her coach provided her with education on the different food groups according to the Newtopia Food Guide, which is based on Canada's Food Guide. The coach explained serving sizes, e.g. 1 cup, ½ cup, tablespoon, etc., and plate portion sizes. Her coach recommended that she increase her daily intake of fruits and vegetables and her weekly intake of fish since these were low in her assessment. Her coach also recommended that she increase her food grown or raised locally or certified organic, and her food grown or raised by her or members of her family since these were marked as zero (0) in her assessment.

Based on her exercise assessment, her coach recommended a strength and cardiovascular exercise program for someone at the low active level. HK was educated on stretching exercises, strength exercises and cardiovascular exercises. Since HK does not have a gym membership, her exercise program involved activities she can do at and around the home.

Based on HK's behaviour subtype, her reasons for losing weight were discussed with her coach and a schedule was made so that HK's weight management can stay on plan. HK also completed the Newtopia genetic test kit for weight and lifestyle management, which was subsequently sent for analysis at the laboratory.

Lastly, HK received the following:
A NewtopiaPed—personal movement tracking sensor,
A NewtopiaScale—wireless scale
A stainless steel water bottle,
A canvas grocery bag, and
A 2-week supply of Newtopia Daily Weight Care and Daily Care for Women.

For the subsequent 2 weeks, HK met with her coach three times weekly to receive further education on nutrition, exercise and well being. HK took 1 pack of Newtopia Daily Weight Care and 1 pack of Newtopia Daily Care for Women daily.

Throughout the course of the Educate Phase, she underwent various exercise assessments: plank time (35 s), sitand-reach (38 in.), push-ups (10) and seated wall squat (60 s). HK was measured for waist, hip and chest diameter. At each session, HK reported any symptoms related to the natural health products she was taking. At the end of week 2, she reported that she was constipated. Her coach recommended that she increase her dietary fibre and to monitor her bowel movements.

She then moved on to the Activate Phase of the program.

Activate Phase

HK's genetic test results were received at the beginning of the Activate Phase of the program. HK was positive for the FTO gene (FTO+−) and MC4R gene (MC4R++), but negative for the DRD2 gene (DRD2−−). Because of the positive FTO gene, HK's exercise program was modified to be more vigorous. As such, the cardiovascular program for HK increased in intensity and her goals were increased also. Because of the positive MC4R gene, HK's diet was modified so that it contained less fat. As such, HK's nutrition program was modified to 1,400 balanced calories. Since her DRD2 gene was negative, HK's well-being assessment remained the disconnected behaviour subtype based on her answers on the Newtopia program assessment.

During the course of the Activate Phase of the program, HK took 2 packs of Newtopia Daily Weight Care daily. Throughout the 35 week course of the Activate Phase of the program, HK gradually lost weight until she reached her goal weight of 135 lbs. Through these weeks, HK received coaching at the Newtopia program site twice weekly. At each session, she received coaching on nutrition, exercise and well-being. Her weight was recorded at each visit and a steady decline, with occasional plateaus, was observed. On a monthly basis, measurements were taken for plank time, sit-and-reach, push-ups and seated wall squat. HK showed an increase in plank time, push-ups and seated wall squats, however, only gained 1 in on the sit-and-reach test.

At the beginning of the Activate phase, Newtopia Iron Support was added to help with HK's fatigue and iron deficiency anemia. She took 2 tablets daily. After 2 weeks, her energy improved gradually and she remained on the product for the length of the program. HK also complained of food cravings and was given Newtopia Appetite Support twice daily. After 1 month on Newtopia Appetite Support, she reported that her cravings were under her control and she discontinued the product.

After 2 weeks in the Activate phase, HK continued to complain of constipation. Her Newtopia coach recommended that she take Newtopia Omega 3 Support twice daily and to increase her water intake. After 2 weeks of this, her bowel movements became more regular and less hard. Due to HK's family history of heart disease, hypertension and elevated cholesterol, she chose to remain on Newtopia Omega 3 Support, which is indicated for the treatment and prevention of these conditions.

After 8 weeks in the Activate phase, Newtopia Thyroid Support, 2 capsules daily, was added to support HK's hypothyroid condition. She reported an increase in energy and that her metabolism was working better. She chose to continue to remain on this product for the remainder of the program.

She then moved on to the Celebrate phase of the program.

Celebrate Phase

After 35 weeks in the Activate phase of the program, HK reached her goal weight of 135 lbs and moved towards sustainable weight management in the Celebrate phase of the program. She met with her coach weekly. At this point in the program, she took 1 pack of Newtopia Daily Weight Care and 1 pack of Newtopia Daily Care for Women. She continued Newtopia Omega 3 support, Iron Support and Thyroid Support. HK remarked that her hormonal symptoms improved with the return of the Newtopia Daily Care for Women product. She continued her exercise program and nutrition program which increase to 1,600 basic calories daily.

Although HK was now at her ideal weight, she continued to suffer from anxiety and was medicated for this condition. She began to take Newtopia Stress and Mood Support 1 capsule daily and remarked an improvement in her over all mood.

She remained in the Celebrate phase of the program for 16 weeks and then moved on to the Liberate phase of the program.

Liberate Phase

HK has completed the Newtopia program and has reached and maintained her goal weight of 135 lbs. She continues to eat a healthy diet, exercise and work on her behaviour. She continues to take Newtopia Daily Care for Women on a daily basis, in addition to Newtopia Iron Support, Omega 3 Support and Thyroid Support. She is a proud Newtopian.

User Case #2

JT completed the Newtopia program assessment at www.newtopia.com on Jun. 12, 2009. Based on the information entered in his assessment, JT is a 39-year-old man (date of birth Mar. 2, 1970), single with no children, with the primary concern of weight management. His current weight and height are 205 lbs and 5'10", respectively, leading to a body mass index (BMI) of 29.4 (overweight). He wishes to lose 35 lbs, with a goal weight of 170 lbs (BMI=24.4). His principal reason for losing weight is to become more physically fit. His assessment also included the following information:

He is a full-time accountant.

He current lifestyle is that of balance between work and home.

He does not have a family physician.

He is comfortable using a computer.

He wishes to take the Newtopia genetic test for weight and lifestyle management.

He has the following servings per day: vegetables (5), fruits (3), 100% whole grains (1), milk and alternatives (0) and meat and alternatives (4).

On a weekly basis, he eats as follows: fish and seafood (7), meat and alternatives (>7), food grown or raised locally or certified organic (>7) and food grown or raised by you or members of your family (3).

He drinks 10 cups of water per day.

He is a non-smoker.

He does not drink alcohol.

He is currently taking vitamins and supplements (Natural Factors brand).

He has food allergies or food intolerances and is able to manage these.

He has not tried to lose weight in the past.

He is currently involved in continuous exercise as follows: vigorous exercise (3-4 times weekly; 31-45 minutes sessions; tennis, kickboxing and mountain climbing) and moderate exercise (3-4 times weekly; 31-45 minutes; brisk walking, yoga and playing golf while walking the course).

He belongs to a gym.

He does not have exercise equipment at home.

He participates in strength activities 1-2 times weekly.

He participates in cardio activities 3-4 times weekly.

He answered "no" to all the exercise PAR-Q questions.

He is currently taking the following medications: sedative (lorazepam) and non-steroidal anti-inflammatory (meloxicam).

He report that he suffers from stress management issues, knee osteoarthritis, exercise fatigue and has a family history of cancer (wishes cancer prevention).

Based on his exercise assessment, he was classified as moderately active.

Based on his well-being assessment, he was classified as having all-or-nothing behaviours with respect to weight management.

Program Review and Educate Phase

Following analysis of JT's answers on the Newtopia program assessment, he was contacted by Newtopia program administrators and scheduled to meet with a sales manager. The sales manager reviewed the Newtopia program assessment with JT, explained the Newtopia program and reviewed any contraindications or cautions with the program. JT thought about the proposal for a week and then enrolled into the Newtopia program. The Newtopia program links its coaches and clients based on synergy. JT was assigned a coach with a specialty in working with all-or-nothing behaviour related to weight management. Newtopia coaches modify their coaching practices based on the well-being subtype of the client. For clients with all-or-nothing behaviours, the coaching method is focused on making a schedule for the client and keeping them on track throughout their weight management program. He then began the Educate Phase of the program.

Educate Phase

His weight was recorded at 205 lbs. Based on his nutritional assessment, his coach recommended a diet of 2,200 basic calories daily. His coach provided him with education on the different food groups according to the Newtopia Food Guide, which is based on Canada's Food Guide. The coach explained serving sizes, e.g. 1 cup, ½ cup, tablespoon, etc., and plate portion sizes. Since his intake of fruits, vegetables and fish was excellent, he was recommended by his coach to continue this eating habit. Since he ate foods locally grown, organically produced and grew some of his own vegetables, we was recommended by his coach to continue doing as such.

Based on his exercise assessment, his coach recommended a strength and cardiovascular exercise program for someone at the moderate active level. JT was educated on stretching exercises, strength exercises and cardiovascular exercises. Since JT has a gym membership, his exercise program involved workouts he can do at the gym. Since he does not have exercise equipment at home, only gym exercises were recommended.

Based on JT's behaviour subtype, his reasons for losing weight were discussed with his coach and a schedule was made so that JT's weight management can stay on plan. JT also completed the Newtopia genetic test kit for weight and lifestyle management, which was subsequently sent for analysis at the laboratory.

Lastly, JT received the following:
A NewtopiaPed—personal movement tracking sensor,
A NewtopiaScale—wireless scale
A stainless steel water bottle,
A canvas grocery bag, and
A 2-week supply of Newtopia Daily Weight Care and Daily Care for Men.

For the subsequent 2 weeks, JT met with his coach three times weekly to receive further education on nutrition, exercise and well being. JT took 1 pack of Newtopia Daily Weight Care and 1 pack of Newtopia Daily Care for Men daily.

Throughout the course of the Educate Phase, he underwent various exercise assessments: plank time (60 s), sit-and-reach (40 in.), push-ups (25) and seated wall squat (60 s). JT was measured for waist, hip and chest diameter. At each session, JT reported any symptoms related to the natural health products he was taking. At the end of week 2, he reported that he was having trouble sleeping. His coach recommended that he take his Newtopia Daily Weight Care at lunch and not at dinner as the green tea in this product could have affected his sleep. This resolved his sleep issue.

He then moved on to the Activate Phase of the program.

Activate Phase

JT's genetic test results were received at the beginning of the Activate Phase of the program. JT was negative for the FTO gene (FTO−−) and MC4R gene (MC4R−−), but positive for the DRD2 gene (DRD2++). Because his DRD2 gene was positive, JT's well-being assessment was modified from the all-or-nothing subtype to the emotional behaviour subtype. People positive for the DRD2 gene tend to have emotional eating patterns. Because JT was negative for the FTO gene, the vigour of his exercise program remained the same; people with positive for the FTO gene require vigorous exercise to lose weight. Because JT was negative for the MC4R gene, his nutrition program remained at 2,200 basic calories daily; people positive for the MC4R gene require less fat in their diet in order to lose weight. JT's coach also had experience in working with emotional subtype clients, therefore, remained a synergistic match with JT and continued to be his coach throughout the program.

During the course of the Activate Phase of the program, JT took 2 packs of Newtopia Daily Weight Care daily. Throughout the 17 week course of the Activate Phase of the program, JT gradually lost weight until he reached his goal weight of 170 lbs. Through these weeks, JT received coaching at the Newtopia site twice weekly. At each session, he received coaching on nutrition, exercise and well-being. His weight was recorded at each visit and a steady decline was observed. On a monthly basis, measurements were taken for plank time, sit-and-reach, push-ups and seated wall squat. JT showed an increase in plank time and push-ups, but no improvement in the seated wall squats and sit-and-reach tests.

After 2 weeks in the Activate Phase of the program, JT reported that his insomnia returned. His coach recommended that he take his Newtopia Daily Weight Care at breakfast (1 pack) and at lunch (1 pack). His coach also recommended that JT take Newtopia Stress and Mood Support twice daily. After 1 week on this regimen, he reported that his sleep significantly improved. JT also suffers from occasional insomnia and reported a decrease in the use of his sleeping medication (lorazepam).

After 10 weeks in the program, JT wanted to increase his energy for a sports competition he was registered for. His coach recommended that he take Newtopia Energy and Exercise Support 2 capsules twice daily. He immediately noticed an increase in energy and his sleep remained unaffected. He successfully completed his sports competition and then discontinued the product.

After the completion of his sporting event, his knee osteoarthritis began to be more bothersome. His coach recommended that he take Newtopia Joint Support: Glucosamine Sulfate 2 capsules twice daily. After 4 weeks on this product, he remarked considerable improvement in his knee pain.

He then moved on to the Celebrate Phase of the program.

Celebrate Phase

After 17 weeks in the Activate Phase of the program, HK reached his goal weight of 170 lbs and moved towards sustainable weight management in the Celebrate Phase of the program. He met weekly with his coach. At this point in the program, he took 1 pack of Newtopia Daily Weight Care and 1 pack of Newtopia Daire Care for Men. He continued Newtopia Joint Support: Glucosamine Sulfate and Newtopia Stress and Mood Support. He has discontinued the use of lorazepam for insomnia and only occasionally takes his non-steroidal anti-inflammatory drug (meloxicam) for knee pain. Since JT complained of stress management issues, he found that the Newtopia Stress and Mood Support product was beneficial for his stress management. He continued his exercise program, but was increased to an advanced level for both strength and cardiovascular training. His nutrition program was increased to 2,400 basic calories daily.

He remained in the Celebrate Phase of the program for 8 weeks and then moved on to the Liberate Phase of the program.

Liberate Phase

JT has completed the Newtopia program and has reached and maintained his goal weight of 170 lbs. He continues to eat a healthy diet, exercise and work on his behaviour. He continues to take Newtopia Daily Care for Men on a daily basis as this assists him with cancer prevention, in addition to Newtopia Joint Support: Glucosamine Sulphate. He is a proud Newtopian.

GENETIC TESTING REFERENCES

1. Frayling T M, Timpson N J, Weedon M N, Zeggini E, Freathy R M, et al. 2007. A common variant in the FTO gene is associated with body mass index and predisposes to childhood and adult obesity. *Science* 316: 889-94
2. Scott L J, Mohlke K L, Bonnycastle L L, Willer C J, Li Y, et al. 2007. A genome-wide association study of type 2 diabetes in Finns detects multiple susceptibility variants. *Science* 316: 1341-5
3. Dina C, Meyre D, Gallina S, Durand E, Korner A, et al. 2007. Variation in FTO contributes to childhood obesity and severe adult obesity. *Nat Genet* 39: 724-6
4. Scuteri A, Sanna S, Chen W M, Uda M, Albai G, et al. 2007. Genome-wide association scan shows genetic variants in the FTO gene are associated with obesity-related traits. *PLoS Genet* 3: e115
5. Gerken T, Girard C A, Tung Y C, Webby C J, Saudek V, et al. 2007. The obesity-associated FTO gene encodes a 2-oxoglutarate-dependent nucleic acid demethylase. *Science* 318: 1469-72
6. Wahlen K, Sjolin E, Hoffstedt J. 2008. The common rs9939609 gene variant of the fat mass- and obesity-associated gene FTO is related to fat cell lipolysis. *J Lipid Res* 49: 607-11
7. Peeters A, Beckers S, Verrijken A, Roevens P, Peeters P, et al. 2008. Variants in the FTO gene are associated with common obesity in the Belgian population. *Mol Genet Metab* 93: 481-4
8. Do R, Bailey S D, Desbiens K, Belisle A, Montpetit A, et al. 2008. Genetic variants of FTO influence adiposity, insulin sensitivity, leptin levels, and resting metabolic rate in the Quebec Family Study. *Diabetes* 57: 1147-50
9. Andreasen C H, Stender-Petersen K L, Mogensen M S, Torekov S S, Wegner L, et al. 2008. Low physical activity accentuates the effect of the FTO rs9939609 polymorphism on body fat accumulation. *Diabetes* 57: 95-101
10. Gonzalez-Sanchez J L, Zabena C, Martinez-Larrad M T, Martinez-Calatrava M J, Perez-Barba M, Serrano-Rios M. 2008. Variant rs9939609 in the FTO gene is associated with obesity in an adult population from Spain. *Clin Endocrinol* (Oxf)
11. Tan J T, Dorajoo R, Seielstad M, Sim X L, Ong R T, et al. 2008. FTO variants are associated with obesity in the Chinese and Malay populations in Singapore. *Diabetes* 57: 2851-7
12. Jess T, Zimmermann E, Kring S I, Berentzen T, Holst C, et al. 2008. Impact on weight dynamics and general growth of the common FTO rs9939609: a longitudinal Danish cohort study. *Int J Obes* (Lond) 32: 1388-94
13. Chang Y C, Liu P H, Lee W J, Chang T J, Jiang Y D, et al. 2008. Common variation in the fat mass and obesity-associated (FTO) gene confers risk of obesity and modulates BMI in the Chinese population. *Diabetes* 57: 2245-52
14. Marvelle A F, Lange L A, Qin L, Adair L S, Mohlke K L. 2008. Association of FTO with obesity-related traits in the Cebu Longitudinal Health and Nutrition Survey (CLHNS) Cohort. *Diabetes* 57: 1987-91
15. Rampersaud E, Mitchell B D, Pollin T I, Fu M, Shen H, et al. 2008. Physical activity and the association of common FTO gene variants with body mass index and obesity. *Arch Intern Med* 168: 1791-7
16. Loos R J, Bouchard C. 2008. FTO: the first gene contributing to common forms of human obesity. *Obes Rev* 9: 246-50
17. Loos R J, Lindgren C M, Li S, Wheeler E, Zhao J H, et al. 2008. Common variants near MC4R are associated with fat mass, weight and risk of obesity. *Nat Genet* 40: 768-75
18. Qi L, Kraft P, Hunter D J, Hu F B. 2008. The common obesity variant near MC4R gene is associated with higher intakes of total energy and dietary fat, weight change and diabetes risk in women. *Hum Mol Genet* 17: 3502-8
19. Adan R A, Tiesjema B, Hillebrand J J, la Fleur S E, Kas M J, de Krom M. 2006. The MC4 receptor and control of appetite. *Br J Pharmacol* 149: 815-27
20. Nargund R P, Strack A M, Fong T M. 2006. Melanocortin-4 receptor (MC4R) agonists for the treatment of obesity. *J Med Chem* 49: 4035-43
21. MacKenzie R G. 2006. Obesity-associated mutations in the human melanocortin-4 receptor gene. *Peptides* 27: 395-403
22. Hinney A, Bettecken T, Tarnow P, Brumm H, Reichwald K, et al. 2006. Prevalence, spectrum, and functional characterization of melanocortin-4 receptor gene mutations in a representative population-based sample and obese adults from Germany. *J Clin Endocrinol Metab* 91: 1761-9
23. Chambers J C, Elliott P, Zabaneh D, Zhang W, Li Y, et al. 2008. Common genetic variation near MC4R is associated with waist circumference and insulin resistance. *Nat Genet* 40: 716-8
24. Tan K, Pogozheva I D, Yeo G S, Hadaschik D, Keogh J M, et al. 2008. Functional characterization and structural modeling of obesity-associated mutations in the Melanocortin 4 Receptor. *Endocrinology*
25. Wang G J, Volkow N D, Fowler J S. 2002. The role of dopamine in motivation for food in humans: implications for obesity. *Expert Opin Ther Targets* 6: 601-9
26. Volkow N D, Wang G J, Telang F, Fowler J S, Thanos P K, et al. 2008. Low dopamine striatal D2 receptors are associated with prefrontal metabolism in obese subjects: possible contributing factors. *Neuroimage* 42: 1537-43

27. Davis C, Levitan R D, Kaplan A S, Carter J, Reid C, et al. 2008. Reward sensitivity and the D2 dopamine receptor gene: A case-control study of binge eating disorder. *Prog Neuropsychopharmacol Biol Psychiatry* 32: 620-8
28. Noble E P. 2003. D2 dopamine receptor gene in psychiatric and neurologic disorders and its phenotypes. *Am J Med Genet B Neuropsychiatr Genet* 116: 103-25
29. Pohjalainen T, Rinne J O, Nagren K, Lehikoinen P, Anttila K, et al. 1998. The A1 allele of the human D2 dopamine receptor gene predicts low D2 receptor availability in healthy volunteers. *Mol Psychiatry* 3: 256-60
30. Thompson J, Thomas N, Singleton A, Piggott M, Lloyd S, et al. 1997. D2 dopamine receptor gene (DRD2) Taq1 A polymorphism: reduced dopamine D2 receptor binding in the human striatum associated with the A1 allele. *Pharmacogenetics* 7: 479-84
31. Noble E P, Noble R E, Ritchie T, Syndulko K, Bohlman M C, et al. 1994. D2 dopamine receptor gene and obesity. *Int J Eat Disord* 15: 205-17
32. Wang G J, Volkow N D, Logan J, Pappas N R, Wong C T, et al. 2001. Brain dopamine and obesity. *Lancet* 357: 354-7
33. Wang G J, Volkow N D, Thanos P K, Fowler J S. 2004. Similarity between obesity and drug addiction as assessed by neurofunctional imaging: a concept review. *J Addict Dis* 23: 39-53
34. Stice E, Spoor S, Bohon C, Small D M. 2008. Relation between obesity and blunted striatal response to food is moderated by TaqIA A1 allele. *Science* 322: 449-52

The invention claimed is:

1. A computer-implementable method for integrated and personalized management of attributes and behavior of an individual for the purpose of disease management and disease prevention operable by one or more computer processors comprising the steps of:
   (a) a capture utility operable by the one or more computer processors capturing and storing in a database any of the attributes and behaviors relating to the individual's specific nutrition, fitness, and genetic evaluation of FTO, MC4R, and DRD2 genes as individual attributes, said captured behaviors being behavioral attributes;
   (b) an analysis engine operable by the one or more computer processors analyzing: the individual attributes to generate categorizations specific to the individual; and the behavioral attributes to generate directions and suggestions for behavior management and weight management, and based upon a combination of the categorizations and the directions and suggestions, defining an individual classification and template personalized for the individual's nutrition, fitness, behavior and genetic evaluation to deliver positive results specific to the individual;
   (c) a program utility operable by the one or more computer processors automatically establishing a unified program specific to the individual based on the individual classification and the template and formed of a plurality of program elements including components, lessons, information, indicators of change, and tools integrating nutrition, fitness, behavior management and genetics and being operable so the individual can select any program element in any order and following selection utilize the unified program, access information about future aspects of the unified program, and forecast future health management goals, and said selection being devoid of any requirement to meet any achievement relating to the content of any program element;
   (d) a coaching platform operable by the one or more computer processors matching a live coach with the individual based on the behavioral attributes, managing virtual real-time coaching by the coach of the individual, and guiding in-part the coach interactions with the individual; and
   (e) on an ongoing basis and in accordance with triggers implemented in the unified program:
      (i) the capture utility receiving new scientific information for disease management and generating new information parameters based thereon that include strategies for disease management and behavior modification specific to the individual, and the new information parameters being integrated in the template and thereby updating the unified program;
      (ii) the capture utility obtaining and storing in the database up-to-date information relating to the individual and the progress of the individual in the unified program as new individual attributes that include new behavioral attributes, and the analysis engine analyzing the new individual attributes and all data of the unified program to assess effectiveness of the unified program, and of coaches, coach matches, and one or more of the program elements to generate an effectiveness analysis; and
      (iii) the program utility applying automatic adjustments to the unified program, and to at least one or more of the program elements, coach matching, coaching approach, unified program presentation, and communications in accordance with: the new individual attributes; the new behavioral attributes; and the effectiveness analysis.

2. The method of claim 1, wherein the individual attributes include at least one or more of: nutrition attributes, fitness attributes, caloric intake, exercise intensity, exercise location, genetics, and behavioural attributes that incorporate one or more of the following: personality traits, emotions, disconnectedness, all or none attitudes, fitness behaviours (being a level of activity from sedentary to very active, regularity and duration of such activity, strength and cardiovascular activities), life goals, work goals, sleep behaviours, food cravings, food intake, reasons and motivations for food intake, energy levels, motivation to exercise, level of sense of self, mental state, mood, smoker or non-smoker, work hours, alcoholic intake, medical conditions that impede or influence behaviours.

3. The method of claim 1, wherein the components include one or more of: educational component; activation component; and celebration component.

4. The method of claim 1, comprising the step of determining the template based upon the permutation of the categorizations.

5. The method of claim 1, comprising the step of, by operation of the coaching platform, managing virtual real-time coaching in part through web-based coaching, based on the individual's unified program.

6. The method of claim 1, comprising the further step of, by operation of the coaching platform, providing the individual with access to an outline of the steps required to achieve any of the individual's nutrition, fitness, genetic evaluation, and weight management objectives defined for the individual in the unified program with one or more of assistance and oversight of the coach.

7. The method of claim 1, comprising the further step of monitoring the progress of the individual relative to nutrition, fitness, genetic evaluation, and weight management objectives defined for the individual in the unified program.

8. A computer-network implementable system for personalizing a nutrition, fitness, behavior, and genetic evaluation program for an individual for the purpose of disease management and disease prevention, the system comprising:
- (a) a network-accessible application server operable to control and coordinate the following:
  - (i) a capture utility operable to capture and store in a database attributes and behaviors relating to the individual's specific nutrition, fitness, and genetic evaluation of FTO, MC4R and DRD2 genes as individual attributes, said captured behaviors being behavioral attributes, and on an ongoing basis the capture utility:
    - (A) receiving from the network-accessible application server new scientific information for disease management and generating new information parameters based thereon that include strategies for disease management and behavior modification specific to the individual; and
    - (B) obtaining and storing in the database up-to-date information relating to the individual and the progress of the individual in a unified program as new individual attributes that include new behavioral attributes;
  - (ii) an analysis engine operable to analyze: the individual attributes to generate categorizations specific to the individual; and the behavioral attributes to generate directions and suggestions for behavior management and weight management, and based upon a combination of the categorizations and the directions and suggestions, defining an individual classification and template personalized for the individual's nutrition, fitness, behavioral and genetic evaluation to deliver positive results specific to the individual, and on an ongoing basis the analysis engine analyzing the new individual attributes and all data of the unified program to assess effectiveness of the unified program, and of coaches, coach matches, and one or more of a plurality of program elements to generate an effectiveness analysis; and
  - (iii) a program utility operable to automatically establish the unified program specific to the individual based on the individual classification and template and formed of the plurality of program elements including components, lessons, information, indicators of change and tools integrating nutrition, fitness, behavior management and genetics, and on an ongoing basis the program utility applies automatic adjustments to the unified program, and at least to one or more of the program elements, coaching approach, unified program presentation, and communications in accordance with: the new individual attributes; the new behavioral attributes; the new information parameters; and the effectiveness analysis; and
- (b) wherein at least one network-connected client is operable to enable the individual to provide the one or more individual attributes and to select any program element in any order and following selection to utilize the unified program, access information about future aspects of the unified program, and forecast future health management goals, said selection being devoid of any requirement to meet any achievement relating to the content of any program element.

9. The system of claim 8, wherein the individual attributes include at least one or more of: nutrition attributes, fitness attributes, caloric intake, exercise intensity, exercise location, and behavioural attributes that incorporate one or more of the following: personality traits, emotions, disconnectedness, all or none attitudes, fitness behaviours (being a level of activity from sedentary to very active, regularity and duration of such activity, strength and cardiovascular activities), life goals, work goals, sleep behaviours, food cravings, food intake, reasons and motivations for food intake, energy levels, motivation to exercise, level of sense of self, mental state, mood, smoker or non-smoker, work hours, alcoholic intake, medical conditions that impede or influence behaviours.

10. The system of claim 8, wherein the components include one or more of: educational component; activation component; and celebration component.

11. The system of claim 8, wherein the permutations of the categorizations determine the template.

12. The system of claim 8, wherein the network-accessible application server includes or defines a computer-implemented coaching platform that is operable to manage virtual real-time coaching of the individual based on the individual's unified program.

13. The system of claim 12 wherein the coaching platform is operable to guide in-part the interaction between the individual and a coach that is a live person selected for that individual, and to manage virtual real-time coaching by the coach of the individual, and to manage web-based coaching, based on the individual's unified program.

14. The system of claim 13, wherein the coach is matched with the individual at least in part based on the behavioural attributes so as to define compatible personality traits between the coach and the individual.

15. The system of claim 14 wherein the coaching platform is operable to provide the individual with access to an outline of the steps required to achieve their nutrition, fitness, genetic evaluation, and weight management program with one or more of assistance and oversight of coach.

16. The system of claim 8, wherein the system is operable to monitor the progress of the individual relative to nutrition, fitness, genetic evaluation, and weight management objectives defined for the individual in the unified program.

17. The method of claim 1, comprising the further step of a tracking utility operable by one or more computer processors continuously transmitting to the capture utility data relating to activities of the individual as new individual attributes and thereby updating the unified program.

18. The method of claim 1 comprising the steps of:
- (a) capturing the individual attributes to include attributes of the individual relating to weight management and behaviours of the individual relating to weight management;
- (b) generating the categorizations based upon the analysis of the individual attributes to include one or more weight management categorizations; and
- (c) automatically establishing the unified program that includes management of weight for the individual, said unified program being formed of the plurality of program elements that further integrates weight management.

19. The system of claim 8 wherein:
- (a) the individual attributes include attributes related to weight management and behaviours relating to weight management;
- (b) the template incorporates one or more elements defining weight management program aspects;
- (c) the unified program integrating weight management; and (d) the unified program includes at least one a program element relating to weight management.

20. The method of claim 1, comprising the step of integrating one of the following in the template and thereby integrating one of the following in the unified program: video games, and virtual worlds.

21. The method of claim 1, comprising the step of a community utility operable by one or more computer processors creating one or more social networks for interaction between the individual and other individuals engaged in other unified programs.

22. The method of claim 1, comprising the steps of: (a) generating group reports of the progress of the groups of individuals having unified programs; and (b) assessing the effectiveness of program templates, coaches, coach matches and other aspects of such unified programs based upon the group reports.

\* \* \* \* \*